US011992508B2

(12) United States Patent
Schmidt et al.

(10) Patent No.: US 11,992,508 B2
(45) Date of Patent: May 28, 2024

(54) MICRONIZED EGGSHELL MEMBRANE PARTICLES AND THE USE THEREOF TO PROMOTE THE HEALING OF WOUNDS

(71) Applicant: BIOVOTEC AS, Oslo (NO)

(72) Inventors: Ralf Schmidt, Oslo (NO); Henri-Pierre Suso, Oslo (NO); Enda Kenny, Kilkenny (IE)

(73) Assignee: BIOVOTEC AS, Oslo (NO)

( * ) Notice: Subject to any disclaimer, the term of this patent is extended or adjusted under 35 U.S.C. 154(b) by 0 days.

(21) Appl. No.: 15/522,441

(22) PCT Filed: Oct. 28, 2015

(86) PCT No.: PCT/EP2015/075041
§ 371 (c)(1),
(2) Date: Apr. 27, 2017

(87) PCT Pub. No.: WO2016/066718
PCT Pub. Date: May 6, 2016

(65) Prior Publication Data
US 2017/0319629 A1     Nov. 9, 2017

(30) Foreign Application Priority Data

Oct. 28, 2014 (GB) .................................... 1419183
Apr. 16, 2015 (GB) .................................... 1506504
Jun. 30, 2015 (GB) .................................... 1511476

(51) Int. Cl.
  *A61K 35/57*     (2015.01)
  *A61K 9/14*      (2006.01)
  (Continued)

(52) U.S. Cl.
  CPC ................ *A61K 35/57* (2013.01); *A61K 9/14* (2013.01); *A61L 15/40* (2013.01); *A61L 15/60* (2013.01);
  (Continued)

(58) Field of Classification Search
  None
  See application file for complete search history.

(56) References Cited

U.S. PATENT DOCUMENTS 3,194,732 A * 7/1965 Neuhauser .............. A61L 15/40
                                                            424/447
3,196,075 A   7/1965 Neuhauser
(Continued)

FOREIGN PATENT DOCUMENTS

BE           677335 A      9/1966
CA           721555 A      11/1965
(Continued)

OTHER PUBLICATIONS

Wound Care Essentials Practice Principle, chapter 8 "Wound Debridement", Ayello et al., p. 295-335, (Year: 2015).*
(Continued)

*Primary Examiner* — Isis A Ghali
(74) *Attorney, Agent, or Firm* — Karen A. LeCuyer; DeWitt LLP

(57) ABSTRACT

The invention provides a particle consisting essentially of micronized ESM and having a mean particle diameter of less than 100 μm for use in promoting the healing of a chronic wound at risk of, or in which there is, (i) an inappropriate level of matrix-metalloproteinase (MMP) activity against extracellular matrix (ECM) proteins and/or peptide growth or differentiation factors, and/or (ii) an excessive inflammatory response. The invention further provides pharmaceutical compositions, wound dressings and implantable medical devices comprising the micronized ESM-containing particles for use in said treatments. The invention still further provides methods for manufacturing the micronized ESM-containing particles and the compositions, dressings and implantable medical devices comprising the same.

13 Claims, 7 Drawing Sheets

(51) Int. Cl.
*A61L 15/40* (2006.01)
*A61L 15/60* (2006.01)
*A61L 26/00* (2006.01)
*A61L 27/36* (2006.01)
*A61L 31/00* (2006.01)
*A61L 31/08* (2006.01)
*A61P 17/02* (2006.01)

(52) U.S. Cl.
CPC ....... *A61L 26/0023* (2013.01); *A61L 26/0057* (2013.01); *A61L 26/008* (2013.01); *A61L 27/3604* (2013.01); *A61L 31/005* (2013.01); *A61L 31/08* (2013.01); *A61P 17/02* (2018.01); *A61L 2300/30* (2013.01); *A61L 2300/404* (2013.01); *A61L 2300/41* (2013.01); *A61L 2300/412* (2013.01)

(56) References Cited

U.S. PATENT DOCUMENTS

| | | | |
|---|---|---|---|
| 3,400,199 | A | 9/1968 | Balassa |
| 3,558,771 | A | 1/1971 | Balassa et al. |
| 3,804,949 | A | 4/1974 | Balassa |
| 5,356,614 | A | 10/1994 | Sharma |
| 5,503,847 | A | 4/1996 | Queen et al. |
| 6,201,164 | B1 | 3/2001 | Wulff et al. |
| 6,541,447 | B1 | 4/2003 | Dawson |
| 6,946,551 | B2 | 9/2005 | Long et al. |
| 7,767,297 | B2 | 8/2010 | Tajima et al. |
| 7,780,994 | B2 | 8/2010 | Lynn et al. |
| 8,173,174 | B2 | 5/2012 | Strohbehn et al. |
| 8,197,852 | B2 | 6/2012 | Strohbehn et al. |
| 8,197,853 | B2 | 6/2012 | Strohbehn et al. |
| 8,211,477 | B2 | 7/2012 | Strohbehn et al. |
| 8,425,943 | B2 | 4/2013 | Strohbehn et al. |
| 8,580,315 | B2 | 11/2013 | Devore et al. |
| 2004/0180025 | A1 | 9/2004 | Long et al. |
| 2004/0180851 | A1 | 9/2004 | Long et al. |
| 2005/0107302 | A1 | 5/2005 | Dawson |
| 2005/0246840 | A1 | 11/2005 | Sano et al. |
| 2006/0159816 | A1 | 7/2006 | Vlad |
| 2007/0178170 | A1 | 8/2007 | Devore et al. |
| 2007/0225220 | A1 | 9/2007 | Ming et al. |
| 2008/0063677 | A1* | 3/2008 | Long ............ A61K 8/982 424/401 |
| 2008/0124381 | A1 | 5/2008 | Barnhart et al. |
| 2008/0146869 | A1 | 6/2008 | Chow et al. |
| 2009/0031691 | A1 | 2/2009 | Tajima et al. |
| 2009/0074879 | A1 | 3/2009 | Braguti |
| 2009/0104173 | A1 | 4/2009 | Strohbehn et al. |
| 2009/0206009 | A1 | 8/2009 | Floh et al. |
| 2010/0254961 | A1 | 10/2010 | Nishio et al. |
| 2010/0266646 | A1 | 10/2010 | Dvorak et al. |
| 2011/0150961 | A1 | 6/2011 | Perry et al. |
| 2013/0035473 | A1 | 2/2013 | Summers et al. |
| 2013/0337080 | A1 | 12/2013 | Wedekind et al. |
| 2013/0344129 | A1* | 12/2013 | Washburn ......... A61K 39/3955 424/445 |
| 2014/0294961 | A1 | 10/2014 | Kato et al. |
| 2014/0348939 | A1* | 11/2014 | Blaine ............ A61K 35/56 424/581 |
| 2018/0325740 | A1 | 11/2018 | Kenny et al. |
| 2020/0030492 | A1 | 1/2020 | Kenny et al. |

FOREIGN PATENT DOCUMENTS

| | | |
|---|---|---|
| CN | 1295848 A | 5/2001 |
| CN | 1432592 A | 7/2003 |
| CN | 1569244 A | 1/2005 |
| CN | 101288669 A | 10/2008 |
| CN | 101317965 A | 12/2008 |
| CN | 101439114 A | 5/2009 |
| CN | 101575771 A | 11/2009 |
| CN | 101697815 A | 4/2010 |
| CN | 101822783 A | 9/2010 |
| CN | 101837094 A | 9/2010 |
| CN | 102517363 A | 6/2012 |
| CN | 103275205 A | 9/2013 |
| CN | 103300357 A | 9/2013 |
| EP | 2020455 A2 | 2/2009 |
| FR | 1348353 A | 1/1964 |
| FR | 2035769 A1 | 12/1970 |
| GB | 949946 | 2/1964 |
| GB | 1251720 | 10/1971 |
| IN | 00315DE2006 A | 8/2007 |
| IN | 01957MU2008 | 3/2010 |
| JP | 63309273 A | 12/1988 |
| JP | 2231426 A | 9/1990 |
| JP | H02231426 A | 9/1990 |
| JP | 5015581 A | 1/1993 |
| JP | 6192443 A | 7/1994 |
| JP | 7138142 A | 5/1995 |
| JP | 7277949 A | 10/1995 |
| JP | 9241146 A | 9/1997 |
| JP | 11228438 A | 8/1999 |
| JP | 2000167036 A | 6/2000 |
| JP | 2002212069 A | 7/2002 |
| JP | 2002249440 A | 9/2002 |
| JP | 2002265350 A | 9/2002 |
| JP | 2003225298 A | 8/2003 |
| JP | 2003246741 A | 9/2003 |
| JP | 2004018471 A | 1/2004 |
| JP | 2005194401 A | 7/2005 |
| JP | 2006069892 A | 3/2006 |
| JP | 3814247 B2 | 8/2006 |
| JP | 2006326018 A | 12/2006 |
| JP | 2007197393 A | 8/2007 |
| JP | 2008007419 A | 1/2008 |
| JP | 4187976 | 11/2008 |
| JP | 2009089858 A | 4/2009 |
| JP | 2013040115 A | 2/2013 |
| JP | 2013216652 A | 10/2013 |
| KR | 20130103406 A | 9/2013 |
| TR | 201006790 A2 | 12/2010 |
| WO | 9951175 A1 | 10/1999 |
| WO | 200170194 A1 | 9/2001 |
| WO | 2004080388 A2 | 9/2004 |
| WO | 2004080428 A2 | 9/2004 |
| WO | 2005023176 A2 | 3/2005 |
| WO | 2005039499 A2 | 5/2005 |
| WO | 2005040228 A2 | 5/2005 |
| WO | 2005107774 A1 | 11/2005 |
| WO | 2009048924 A1 | 4/2009 |
| WO | 2010006260 A1 | 1/2010 |
| WO | 2010086616 A1 | 8/2010 |
| WO | 2010122490 A2 | 10/2010 |
| WO | 2012036645 A2 | 3/2012 |
| WO | 2012112410 A2 | 8/2012 |
| WO | 2014028327 A1 | 2/2014 |
| WO | 2014190227 A1 | 11/2014 |
| WO | 2015009256 A1 | 1/2015 |
| WO | 2015058790 A1 | 4/2015 |
| WO | 2016066718 A1 | 5/2016 |

OTHER PUBLICATIONS

Hwang et al.; "Poly(ethylene glycol) Cryogels as Potential Cell Scaffolds: Effect of Polymerization Conditions on Cryogel Microstructure and Properties"; J. Mater. Chem.; 20; pp. 345-351; (2010).

Loh et al.; "Three-Dimensional Scaffolds for Tissue Engineering Applications: Role of Porosity and Pore Size"; Tissue Engineering: Part B, 19(6); pp. 485-501; (2013).

Murphy et al.; "Understanding the Effect of Mean Pore Size on Cello Activity in Collagen-glycosaminoglycan Scaffolds"; Cell Adhesion & Migration; 4:3; pp. 377-381; (2010).

Ratanavaraporn et al.; "Effects of Acid Type on Physical and Biological Properties of Collagen Scaffolds"; J. Biomater. Sci. Polymer Edn., 19(7); pp. 945-952; (2008).

Yannas et al.; "Synthesis and Characterization of a Model Extracellular Matrix that Induces Partial Regeneration of Adult Mammalian Skin"; Proc. Natl. Acad. Sci. USA; 86; pp. 933-937; (1989).

(56) References Cited

OTHER PUBLICATIONS

Balaz, Matej; "Eggshell Membrane Biomaterial as a Platform for Applications in Materials Science"; Acta Biomaterialia; 10; pp. 3827-3843; (2014).
Chen et al.; "Preparation and Characterization of Polyurethane/soluble Eggshell Membrane Nanofibers"; Bio-Medical Materials and Engineering; 24; pp. 1979-1989; (2014).
CN101317965 A English Abstract; Sep. 23, 2015; 1 page.
Eming et al.; "Inflammation in Wound Repair: Molecular and Cellular Mechanisms"; Journal of Investigative Dermatology; 127; pp. 514-525; (2007).
GB1419183.7 Search Report, dated Jun. 30, 2015 6 pages.
International Search Report and Written Opinion; International Application No. PCT/EP2015/075041; International Filing Date Oct. 28, 2015; dated Apr. 19, 2016; 17 pages.
Johnson, et al.; "Randomized, Controlled Trial of Topical Exit-Site Application of Honey (Medihoney) versus Mupirocin for the Prevention of Catheter-Associated Infections in Hemodialysis Patients"; J AM Soc Nephrol; 16; pp. 1456-1462; (2005).
JPH02231426 A English Asbstract; 1 page; Sep. 23, 2015.
Yang et al.; "Egg Membrane as a New Biological Dressing in Split-Thickness Skin Graft Donor Sites: A Preliminary Clinical Evaluation"; Chang Gung Med J; 26(3); pp. 153-158; (2003).
Benson et al.; "Effects of Natural Eggshell Membrane (NEM) on Cytokine Production in Cultures of Peripheral Blood Mononuclear Cells: Increased Suppression of Tumor Necrosis Factor-Alpha Levels After In Vitro Digestion"; J. Med Food; 14(4); pp. 360-368; (2012).
Gibson et al.; "MMPs Made Easy"; Wounds International; 1(1); pp. 1-6; (2009) available from http://www.woundsinternational.com.
Holmes et al.; "Collagen-Based Wound Dressings for the Treatment of Diabetes-Related Foot Ulcers: a Systematic Review"; Diabetes, Metabolic Syndrome and Obesity: Targets and Therapy; 6; pp. 17-29; (2013).
Kim et al.; "Coaxially Electrospun Micro / Nanofibrous Poly(E-caprolactone) / Eggshell-Protein Scaffold"; Bioninsp. Biomim.; 3; 9 pages; stacks.iop.org/BB/016006; (2008).
Mishra et al.; "Manufacturing Techniques of Orally Dissolving Films"; Pharmaceutical Technology; 35(1); pp. 1-4; (2011).
O'Brien, Fergal J., "Influence of Freezing Rate on Pore Structure in Freeze-dried Collagen-GAG Scaffolds"; Biomaterials; 25(6); pp. 1077-1086; (2004).
O'Brien, Fergal J.; "The Effect of Pore Size on Cell Adhesion in Collagen-GAG Scaffolds"; Biomaterials; 26(4); pp. 433-441; (2005).
Ohto-Fujita et al.; "Hydrolyzed Eggshell Membrane Immobilized on Phosphorylcholine Polymer Supplies Extracellular Matrix Environment for Human Dermal Fibroblasts"; Cell Tissue Res; 345; pp. 177-190; (2011).
Qin, Yimin; "Review_Aliginate Fibres: An Overview of the Production Processes and Applications in Wound Management"; Polymer International; 57; pp. 171-180; (2008).
Ruff et al.; "Reduction of Pro-Inflammatory Cytokines in Rats Following 7-day Oral Supplementation with a Proprietary Eggshell Membrane-Derived Product"; Modern Research in Inflammation; 3(1); pp. 19-25; (2014).
Tan et al.; "A Scanning and Transmission Electron Microscopic Study of the Membranes of Chicken Egg"; Histol Histopath; 7; pp. 339-345; (1992).
World Union of Wound Healing Societies (WUWHS); Principles of Best Practice: Wound Infection in Clinical Practice; An International Consensus; London: MEP Ltd; 12 Pages; (2008) Available from www.mepltd.co.uk.
Yi et al.; "Soluble Eggshell Membrane Protein: Preparation, Characterization and Biocompatibility"; Biomaterials; 25; pp. 4591-4599; (2004).
Cordeiro et al.; "Recent Patents on Eggshell: Shell and Membrane Applications"; Recent Patents on Food, Nutritiion & Agriculture; 3; pp. 1-8; (2011).
Ruff et al.; "Eggshell Membrans: A Possible New Natural Therapeutic for Joint and Connective Tissue Disorders. Results from Two Open-Label Human Clinical Studies"; Clinical Interventions in Aging; 4; pp. 235-240; (2009).
Ruff et al.; "Safety Evaluation of a Natural Eggshell Membrane-Derived Product"; Food and Chemical Toxicology; 50; pp. 604-611; (2012).
Feng Yi et al.; "Soluble Eggshell Mebrane Protein: Antibacterial Property and Biodegradability"; Journal of Wuhan University of Technology-Mater. Sci. Ed.; Sum. 75, vol. 22, No. 1, pp. 117-119; (2007).
Ngan, V.; "Leg Ulcer"; DermNet NZ [Online]; Retrieved online Sep. 9, 2020 at https://dermnetnz.org/topics/leg-ulcer/; 2020; 7 pages.
Park, J. et al.; "Evaluation of bone healing with eggshell-derived bone graft substitutes in rat calvaria: A pilot study"; Journal of Biomedical Materials Research, vol. 87, Issue No. 1; 2008; pp. 203-214.
Sharma, A. et al.; "Efficacy of supermacroporous poly(ethylene glycol)-gelatin cryogel matrix for soft tissue engineering applications"; Materials Science and Engineering C, vol. 47; 2015; pp. 298-312.
Anonymous; "Wound Care"; DeKalb Regional Medical Center Online Article, retrieved from [http://dekalbregional.com/dekalb-regional-medical-center/woundcare] on Feb. 8, 2021; 2021; 3 pages.
Gooyit, M. et al.; "A Chemical Biological Strategy to Facilitate Diabetic Wound Healing"; ACS Chemical Biology, vol. 9, Issue No. 1; 2014; pp. 105-110; doi: 10.1021/cb4005468.
Manna, B. et al.; "Wound Debridement"; StatPearls [Internet]; Treasure Island, FL; PMID: 29939659; Bookshelf ID: NBK507882; PMID: 29939659; 2020; 6 pages.
Tkalcevic, V. et al.; "Differential Evaluation of Excisional Non-occluded Wound Healing in db/db Mice"; Toxicologic Pathology, vol. 37, Issue No. 2; 2009; pp. 183-192.
Yang, M. et al.; "Thermosensitive Injectable Chitosan/Collagen/β-Glycerophosphate Composite Hydrogels for Enhancing Wound Healing by Encapsulating Mesenchymal Stem Cell Spheroids"; ACS Omega, vol. 5, Issue No. 33; 2020; pp. 21015-21023.
Schultz, G. et al; "Wound bed preparation: a systematic approach to wound management"; Wound Repair and Regeneration, vol. 11, Supplement 1; 2003; S-1-S-28; doi: 10.1046/j.1524-475x.11.s2.1.x.

* cited by examiner

MICRONIZED EGGSHELL MEMBRANE PARTICLES AND THE USE THEREOF TO PROMOTE THE HEALING OF WOUNDS

CROSS REFERENCE TO RELATED APPLICATIONS

This application is a National Stage application of PCT/EP2015/075041, filed Oct. 28, 2015, which claims the benefit of GB 1419183.7 filed Oct. 28, 2014, GB 1506504.8, filed on Apr. 16, 2015 and GB 1511476.2, filed on Jun. 30, 2015, all of which are incorporated by reference in their entirety herein.

The present invention relates generally to the field of the treatment of wounds in order to promote the healing thereof. More specifically the present invention provides eggshell membrane (ESM) microparticles and nanoparticles that have been found to display certain properties when present in or on a wound that make them particularly advantageous in promoting wound healing, including the healing of chronic wounds, including burns, at risk of, or in which there is, an inappropriate level of MMP activity against ECM proteins and/or peptide growth or differentiation factors, and/or an excessive inflammatory response. The invention further provides pharmaceutical compositions, wound dressings and implantable medical devices comprising the micronized ESM particles for use in said treatments. The invention still further provides methods for manufacturing the micronized ESM particles and the compositions, dressings and implantable medical devices comprising the same.

Wounds, a breach in the integrity of, or denudement of, a tissue, commonly the skin, are an inevitable occurrence in the lives of humans and other animals. Wounds may be caused surgically, by physical injury (e.g. mechanical injuries; thermal injuries, for instance those resulting from excessive heat or cold; electrical injuries, for instance those caused by contact with sources of electrical potential; and radiation damage caused, for example, by prolonged, extensive exposure to infrared, ultraviolet or ionizing radiations) or by a spontaneously forming lesion such as a skin ulcer (e.g. a venous, diabetic or pressure ulcer), an anal fissure, a mouth ulcer and acne vulgaris.

In the medical fields, wounds are typically defined as either acute or chronic. Acute wounds are wounds that proceed orderly through the three recognised stages of the healing process following haemostasis (i.e. the inflammatory stage, the proliferative stage and the remodelling phase) without a protracted timecourse. Chronic wounds are defined as those which fail to heal or where there is excessive skin loss such as through burns. Such wounds do not complete the ordered sequence of biochemical events of the healing process because the wound becomes stalled in one of the healing stages. Commonly, chronic wounds are stalled in the inflammatory phase. Chronic wounds are a major source of morbidity for patients.

The primary goal of wound healing treatments is to close or reform the outer layers of the wounded tissue, e.g. the epidermis in the context of a skin wound, so as to prevent blood loss or infection of the underlying tissues. For acute wounds this can be relatively straightforward with treatment placing great reliance on the natural healing processes of the wounded subject. However, in the case of chronic wounds, those healing processes are not functioning as they should and so a key goal in their treatment is to enhance and augment the response of the body and to assist the body in regeneration of damaged or broken tissues.

Conventional wound healing treatments focus on the haemostasis stage, absorption of excess exudate and maintenance of a sterile barrier to prevent infection whilst the skin lesion heals. Conventional products may also assist in maintaining topical pharmacological products in situ such as antibiotic and steroid creams and prevent them from being eroded from contact with clothing etc. Advanced wound healing products may share these features also, but their primary role is the maintenance of a moist healing environment. For optimal wound healing, it is critical that the wound bed is moist but not overly wet which will result in maceration of the surrounding skin as well as the wound bed. Advanced wound-care products may also contain pharmacological products to assist wound healing such as antibiotics or growth factors.

However, a major reason for development of chronic wounds is an imbalance in the wound repair cycle following haemostasis and these prior art approaches do not focus on those other healing stages specifically, i.e. the inflammation, proliferation and tissue remodelling (e.g. re-epithelialisation) stages.

As such, a wound healing treatment which is able to deal with an excessive inflammatory response in the wound would be advantageous. Moreover, it has recently been shown that imbalances in the healing process during the inflammatory phase can lead to overproduction and/or overactivity of proteases, e.g. MMPs (e.g. MMP-2, MMP-8 and MMP-9), collagenase, elastase and plasmin in the wound bed. This leads to destruction of newly synthesized extracellular matrix (ECM) and destruction of endogenously produced growth and differentiation factors within the wound bed. This imbalance can be addressed by the addition of stimulatory growth factors such as Regranex™ (recombinant human PDGF), however, even in this case the exogenous PDGF can be quickly inactivated by proteases. Another way this can be addressed is through the addition of proteins or other materials which preferentially bind the proteases and divert them from proteolysis of the ECM constituents and protein growth factors such as PDGF. Such products include collagen based materials such as Promogran™ and complex ECM based materials such as porcine small intestine sub-mucosa (Oasis™) However, these products are derived from a mammalian source, usually bovine or porcine and are at risk from transfer of certain viruses or TSEs. Accordingly, a non-mammalian source would be preferable.

The remodelling of ECM by proteases, e.g. MMPs, is also observed during the processes of angiogenesis, e.g. in neoplasms (tumours), and of metastasis of malignant neoplasms. In these processes proteases are believed to at least partially degrade the ECM surrounding the cells of the growing blood vessel or neoplasm and this allows such cells the freedom to move to create the walls of the growing blood vessel or a secondary malignant neoplasm in a new location. Angiogenesis is a normal physiological process, but in growing neoplasms the process is also utilised to provide a blood capillary network for the neoplasm thereby permitting further growth. Agents which are able to inhibit proteases in these physiological contexts would have the potential to combat neoplasms (in particular after surgical excision) and prevent metastasis.

Recently, it has been shown that intact hen eggshell membrane (ESM) can be used to promote wound healing when placed as an intact film over damaged skin (Yang, J-Y et al. 2003. Chang Gung Med J).

ESM is a complex bi-layered protein-rich fibrous structure found in an avian egg between the albumen and the eggshell. Studies have shown that such membranes contain approximately 90% protein by weight (including collagen, elastin, fibronectin peptide growth factors, ovotrasferrin, lysl oxidase and lysozyme) and desmosine, isodesmosine and glycosaminoglycans (e.g. dermatane sulphate, chondroitin sulphate and hyaluronic acid). ESM can readily be separated from the eggshell and the internal components of the egg by a variety of mechanical means to produce an essentially pure preparation of ESM.

When placed as an intact sheet over a skin wound ESM functions as a semi-permeable membrane and allows moisture vapour transmission and so manages moisture within the wound bed. Its characteristics are similar to synthetic materials such as Biobrane™. However, intact ESM in sizes that are appropriate for use in wound healing contexts is difficult to prepare in commercially viable amounts. Intact ESM requires manual preparation to maintain a useable size and even then it would need to be applied as a mosaic of individual membranes. During processing the delicate material requires separation from residual bound calcium and associated egg white components and either aseptic processing or terminal sterilisation. Process and quality control sufficient for manufacture of a medical product in such contexts are, as a result, not technically or economically feasible.

Powders of ESM of 100-500 μm have also been proposed for the treatment of certain wounds via a topical route of administration (WO 2004/080428). The basis for this proposal is not clear and nor is evidence of successful treatment provided.

Powders of ESM of 100-500 μm have also been proposed for the treatment of pain and inflammation associated with arthritis and other inflammatory conditions via a systemic, in particular oral, route of administration (U.S. Pat. No. 8,580, 315).

Smaller ESM particles have been described and suggested for use in treatments for acute skin wounds and as replacement skin grafts for fresh wounds (U.S. Pat. Nos. 3,196,075 and 3,194,732). Any effects on the inflammatory phase of a chronic wound are not disclosed and a utility in the context of chronic wounds is not suggested.

It has now been found surprisingly that micronized ESM particles with an average particle diameter of less than 100 μm have a particular repertoire of properties that make them especially advantageous in the treatment of chronic wounds, including burns, at risk of, or in which there is, (i) an inappropriate level of matrix-metalloprotease (MMP) activity against ECM proteins and/or peptide growth or differentiation factors, in particular; and/or (ii) an excessive inflammatory response in order to promote healing thereof.

These properties include (i) the ability to reduce the degradation of ECM and/or peptide growth or differentiation factors in a wound, e.g. by reducing the activity of MMPs in a wound against ECM proteins and/or peptide growth or differentiation factors; (ii) an anti-inflammatory effect; (iii) an antimicrobial effect; (iv) the ability to promote the de novo formation of tissue by promoting migration of the cells of the wound tissue into the wound and/or the proliferation and/or differentiation of those cells e.g. through an ability to act as a scaffold for those cells; (v) the ability not to interfere with the maintenance of a moist healing environment and (vi) amenability to processing within carrier matrices (e.g. gel matrices, including hydrogel and hydrocolloid gels).

Thus, in a first aspect there is provided a method to promote the healing of a chronic wound at risk of, or in which there is, (i) an inappropriate level of MMP activity against ECM proteins and/or peptide growth or differentiation factors, and/or (ii) an excessive inflammatory response, wherein one or more particles consisting essentially of micronized eggshell membrane (ESM) and having a mean particle diameter of less than 100 μm are applied to said wound in an amount sufficient to promote the healing of the wound.

Alternatively, this aspect of the invention provides a particle consisting essentially of micronized ESM and having a mean particle diameter of less than 100 μm for use in promoting the healing of a chronic wound at risk of, or in which there is, (i) an inappropriate level of MMP activity against ECM proteins and/or peptide growth or differentiation factors, and/or (ii) an excessive inflammatory response.

Alternatively still, this aspect of the invention provides the use of a particle consisting essentially of micronized ESM and having a mean particle diameter of less than 100 μm in the manufacture of a medicament for use in promoting the healing of a chronic wound at risk of, or in which there is, (i) an inappropriate level of MMP activity against ECM proteins and/or peptide growth or differentiation factors, and/or (ii) an excessive inflammatory response.

In certain embodiments the wound is a wound at risk of, or in which there is, an inappropriate, i.e. excessive, level of MMP-2, MMP-8 and/or MMP-9, activity against ECM proteins and/or peptide growth or differentiation factors. In other embodiments the wound is a wound at risk of, or in which there is, an inappropriate, i.e. excessive, level of overall MMP activity. In other embodiments the wound is a wound at risk of, or in which there is, an inappropriate, i.e. excessive, level of ECM and/or peptide growth or differentiation factor degradation. Wounds with these features may be identified with the above described methods for measuring ECM protein and/or peptide growth or differentiation factor degradation or for monitoring overall or specific MMP activity against ECM proteins and/or peptide growth or differentiation factors or wound substrates in general.

In certain embodiments the target wound is, or is also, a wound at risk of becoming, or which is, inflamed, e.g. a wound which contains immune cells (e.g. macrophages, monocytes, mast cells and/or neutrophils) and/or inappropriate, i.e. excessive, levels of pro-inflammatory markers (e.g. those disclosed herein) and/or inappropriate, i.e. insufficient, levels of anti-inflammatory markers (e.g. those disclosed herein).

In the following, for the sake of brevity and clarity, a reference to a "wound" or a "target wound" is a reference to the above mentioned chronic wounds unless context specifically dictates otherwise.

By promotion of wound healing it is meant that the treatment of a wound with a micronized ESM-containing particle as defined herein accelerates the healing process of the wound in question (i.e. the progression of the wound through the three recognised stages of the healing process). The acceleration of the healing process may manifest as an increase in the rate of progression through one, two or all of the healing stages (i.e. the inflammatory stage, the proliferative stage and/or the remodelling phase). If the wound is stalled in one of the healing stages the acceleration might manifest as the restarting of the linear, sequential healing process after the stall. In other words, the treatment shifts the wound from a non-healing state to a state where the wound begins to progress through the healing stages. That progression after the restart may be at a normal rate or even a slower rate compared with the rate a normal acute wound would heal. Promotion of wound healing may also be considered to amount to the prevention of a deceleration the healing process of the wound in question. A deceleration of the healing process may manifest as a decrease in the rate of progression through one, two or all of the healing stages. If the wound is restarting of the linear, sequential healing process after a stall deceleration might manifest as a return to being stalled in one of the healing stages. In other words, the treatment prevents a wound from shifting from a healing state to a non-healing state. The promotion of wound healing may further be considered to amount to the treatment of an existing wound or the prevention of the growth of an existing wound and/or an existing healing wound becoming a poorly healing or chronic wound.

The treatment of a target wound with a micronized ESM-containing particle (which term is used herein interchangeably with "ESM particle" and "particle of ESM") as defined herein in order to promote healing may reduce or limit the activity of MMPs in the wound against ECM proteins and/or peptide growth or differentiation factors. Accordingly the invention can be considered to encompass a method to promote the healing of a wound in which the activity of MMPs in the wound against ECM proteins and/or peptide growth or differentiation factors is reduced or limited, wherein one or more ESM particles as defined herein is applied to said wound in an amount sufficient to reduce or limit the activity of MMPs in a wound against ECM proteins and/or peptide growth or differentiation factors.

MMP-2 (also referred to as 72 kDa type IV collagenase or gelatinase A), MMP-8 (also referred to as neutrophil collagenase or PMNL collagenase) and/or MMP-9 (also referred to as 92 kDa type IV collagenase, 92 kDa gelatinase or gelatinase B) are commonly found in wounds, especially chronic wounds, and in preferred embodiments it is the activity of these MPPs specifically against ECM proteins and/or peptide growth or differentiation factors that is reduced.

In certain embodiments the activity of MMPs in a wound against ECM proteins and/or peptide growth or differentiation factors is reduced or limited to a level that is not detrimental to the healing process of wound undergoing treatment. This reduction may be observed as a reduction in the level of ECM protein (e.g. collagen and elastin) and/or peptide growth or differentiation factor fragments in the wound (or wound fluid), which in turn are an indication of the degradation of these proteins, and which may be detected by routine techniques including immunohistochemistry/immunocytochemistry techniques and/or biomolecule (e.g. protein) stains and dyes or by analysing wound fluid with chromatographic techniques. Limitation may be observed as the maintenance of such levels.

Each wound will require a different (e.g. reduced) level of MMP activity against ECM proteins and/or peptide growth or differentiation factors and even over time the requirements of the same wound in this regard may differ. While this may be determined by the skilled person without undue burden if necessary, a key advantage of the micronized ESM-containing particles disclosed herein is that it is relatively easy to achieve an effective level of MMP inhibition and as such onerous dose optimisation is not necessary as routine. Indeed, in most cases any reduction in MMP activity caused by the ESM particles defined herein will be effective in promoting wound healing.

Expressed numerically, following application of the micronized ESM-containing particles of use in the invention to the wound undergoing treatment, MMP activity against ECM proteins and/or peptide growth or differentiation factors in a wound (or overall ECM protein and/or peptide growth or differentiation factor degradation) will preferably be reduced by at least 5%, e.g. at least 10%, 15%, 20%, 25%, 30%. In certain embodiments it may be necessary to maintain some level of MMP activity against ECM proteins and/or peptide growth or differentiation factors (or overall ECM protein and/or peptide growth or differentiation factor degradation), and in such embodiment the reduction in MMP activity against ECM proteins and/or peptide growth or differentiation factors (or overall ECM protein and/or peptide growth or differentiation factor degradation) is no more than 90%, e.g. no more than 80%, 70%, 60%, 50%, 40%, 30%, 25%, 20%, 15%, 10% or 5%. Any and all range endpoints derivable from the combination of any of these values are specifically contemplated.

Without wishing to be bound by theory, the reduction or limitation in MMP activity against ECM proteins and/or peptide growth or differentiation factors (or overall ECM protein and/or peptide growth or differentiation factor degradation) may be on account of a number of mechanisms. This may include, but not be limited to, direct inhibition of the wound MMPs, absorption and deactivation of the wound MMPs, titrating out of the wound MMPs by providing alternative/excess substrate, inhibiting enzymes involved in wound MMP activation (e.g. serine proteases, including plasmin, neutrophil elastase and mast cell chymase), upregulating endogenous inhibitors of MMPs in the wound (e.g. TIMPs; tissue inhibitors of metalloproteinases) inhibiting the expression and/or secretion of MMPs by the cells of the wound and/or inflammatory cells, e.g. monocytes, macrophages, neutrophils and mast cells. The skilled person would be able to measure such effects in a wound without undue burden with routine analytical techniques, some of which are available commercially. The percentage reductions recited above apply in these contexts.

The reduction or limitation in MMP activity against ECM proteins and/or peptide growth or differentiation factors may be reflected in a reduction in or maintenance of overall MMP activity in the wound undergoing treatment. Overall MMP activity is a measure of all MMP activity against all wound substrates. Overall MMP activity can be measured without undue burden with routine analytical techniques, some of which are available commercially. Expressed numerically, following application of the ESM particle of use in the invention to the wound undergoing treatment overall MMP activity in the wound will preferably be reduced by at least 5%, e.g. at least 10%, 15%, 20%, 25%, 30%.

In certain embodiments it may be necessary to maintain some level of overall MMP activity, and in particular MMP activity against ECM proteins and/or peptide growth or differentiation factors, and in such embodiments the reduction in overall MMP activity, in particular MMP activity against ECM proteins and/or peptide growth or differentiation factors is no more than 90%, e.g. no more than 80%, 70%, 60%, 50%, 40%, 30%, 25%, 20%, 15%, 10% or 5%. Any and all combinations of range endpoints derivable from any of these values are specifically contemplated.

In other embodiments the overall activity of particular MMPs are considered, e.g. MMP-2, MMP-8 and/or MMP-9. In these embodiments overall MMP activity is the activity of the specific MMP in question against all wound substrates.

In one embodiment the method of the invention may comprise a step in which the subject will be diagnosed as having a wound that is at risk of inappropriate, i.e. excessive, levels of MMP activity against ECM proteins and/or peptide growth or differentiation factors (or overall levels of MMP activity) or which would benefit from having MMP activity against ECM proteins and/or peptide growth or differentiation factors (or overall levels of MMP activity) reduced or limited (e.g. maintained). In other embodiments the method of the invention may comprise a step in which the subject will be diagnosed as having a wound that is at risk of inappropriate, i.e. excessive, levels of ECM protein and/or peptide growth or differentiation factor degradation.

In a further embodiment, the method of the invention may comprise, following application of the ESM particles of use in the invention to the wound, a step in which the degradation of ECM proteins and/or peptide growth or differentiation factors is monitored, and/or the MMP activity against ECM proteins and/or peptide growth or differentiation factors is monitored and/or overall MMP activity is monitored. In other embodiments MMPs 2, 8 and/or 9 are considered in place of MMPs in general. Alternatively or additionally the method of the invention may comprise, following application of the ESM particles of use in the invention to the wound, a step in which a clinical indicator of the wound (for example wound size (depth and/or area), healing time, general discomfort or pain in the wound or surrounding tissue) is monitored. These monitoring steps may involve comparison to the same metric immediately prior to application of the ESM particles of use in the invention to the wound or another point even earlier in the subject's treatment.

In this aspect a "sufficient (or effective) amount" of the ESM particles of use in the invention is that amount of ESM particles as defined herein which results in the effects on MMP activity and the degradation of ECM proteins and/or peptide growth or differentiation factors effects described above and thereby promotes the healing of the wound. The skilled man would easily be able to determine what an effective (sufficient) amount of ESM particles would be on the basis of routine dose response protocols and, conveniently, the routine techniques for assessing MMP activity and the degradation of ECM proteins and/or peptide growth or differentiation factors discussed above and as exemplified in Example 3.

The treatment of a target wound with an ESM particle as defined herein in order to promote healing may, or may also, reduce or limit inflammation in the wound. Accordingly the invention can be considered to encompass a method to promote the healing of a wound in which inflammation in the wound is, or is also, reduced or limited, wherein an ESM particle as defined herein is applied to said wound in an amount sufficient to reduce or limit inflammation therein.

Inflammation in a wound may be seen as erythema, swelling, local warmth, odema and/or pus. A reduction in the anatomical extent and/or intensity of one or more of these signs of inflammation amounts to a reduction in inflammation. The maintenance of, or prevention of an increase in, the anatomical extent and/or intensity of one or more of these signs of inflammation amounts to a limitation in inflammation.

Alternatively, or in addition, the levels or activity of pro-inflammatory and/or anti-inflammatory markers, e.g. cytokines and chemokines, and/or immune cells in the wound may be measured, e.g. in a sample of wound tissue and/or in a sample from the wound interior. More specifically, the levels or activity of TNFα, IL-1, IL-6, NF-κB, ROS, histamine, macrophages, monocytes, mast cells and/or neutrophils may be measured. This may, for example, be by immunoassay or flow cytometry of a wound sample or suitable activity assays.

A reduction in the levels or activity of one or more pro-inflammatory markers and/or immune cells in the wound sample may be taken to amount to a reduction in inflammation in the wound. Similarly, an increase in the level or activity of one or more anti-inflammatory markers in a wound sample may be taken to amount to a reduction in the inflammation in a wound. The maintenance of, or prevention of an increase in, the level or activity of one or more pro-inflammatory markers and/or immune cells or maintenance of, or prevention of a decrease in, the level or activity of one or more the anti-inflammatory markers in the wound sample may be taken to amount to a limitation of the inflammation in the wound.

In this aspect a "sufficient (or effective) amount" of the ESM particles of use in the invention is that amount of ESM particles which results in the effects on the inflammation in a wound described above, in particular the effects on pro- and/or anti-inflammatory marker levels or activities and/or immune cell levels or activities, and thereby further promotes the healing of the wound. The skilled man would easily be able to determine what an effective (sufficient) amount of ESM particles would be on the basis of routine dose response protocols and, conveniently, the routine techniques for assessing wound inflammation, as discussed above and as exemplified in Example 2.

In one embodiment the method of the invention may comprise a step in which the subject will be diagnosed as having a wound that is, or is also, at risk of developing inflammation or would benefit from having inflammation in it treated (i.e. reduced or limited).

In a further embodiment, the method of the invention may comprise, following application of the ESM particles of use in the invention to the wound, a step in which the extent of the inflammation in the wound is monitored. These monitoring steps may involve comparison to the same metric immediately prior to application of the ESM particles of use in the invention to the wound or another point even earlier in the subject's treatment.

In certain embodiments the ESM particle of use in the invention has a mean particle diameter of less than 95 µm, e.g. less than 90, 85, 80, 75, 70, 65, 60, 55, 50, 45, 40, 35, 30, 25, 20, 15, 10, 5, or 1 µm, e.g. less than 900, 850, 800, 750, 700, 650, 600, 550, 500, 450, 400, 350, 300, 250, 200, 150, 100, 50, 10, 5 or 1 nm.

In certain embodiments the ESM particle of use in the invention also has a mean particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 µm, e.g. equal to or greater than 5, 10, 15, 20, 25, 30, 35, 40, 45, 50, 55, 60, 65, 70, 75, 80, 85, 90 or 95 µm. Any and all range endpoints derivable from the combination of any of these values are specifically contemplated.

The particle may be any three-dimensional shape. It may be essentially symmetric or asymmetric. It may be essentially spherical, prismatoidal or cylindrical. It may be essentially irregular or regular or have regions of both. It may be angular, rounded or tapered or have regions thereof. In certain embodiments the particle has one length dimension that is significantly greater than the others and so may be referred to as, for example, rod-shaped, needle-shaped or fibrous (rods, needles or fibres) and may be qualified as cylindrical or prismatoidal (e.g. cuboidal) depending on the cross-sectional shape substantial perpendicular to the dimension of significantly greater length.

In certain embodiments the particle of use in the invention has an aspect ratio between a first length dimension and a second length dimension arranged perpendicular thereto of at least 1.5 (first length dimension: second length dimension), e.g. at least 2, 3, 4, 5, 6, 7, 8, 9, 10, 12, 14, 16, 18, 20, 25, 30, 35, 40, 45, 50, 55, 60, 65, 70, 80, 90 or 100. In other embodiments the particle of use in the invention has an aspect ratio between a first length dimension and a second length dimension arranged substantially perpendicular thereto of no greater than 2 (first length dimension: second length dimension), e.g. no greater than 3, 4, 5, 6, 7, 8, 9, 10, 12, 14, 16, 18, 20, 25, 30, 35, 40, 45, 50, 55, 60, 65, 70, 80, 90 or 100. Any and all range endpoints derivable from the combination of any of these values are specifically contemplated, e.g. the particle of use in the invention may have an aspect ratio of any of 5, 6, 7, 8, 9 or 10 to any of 20, 25, 30, 35, 40, 45, 50, 55, 60, 65 or 70.

In these embodiments the first length dimension is the longest length dimension in the particle and may be termed the longitudinal dimension. The second length dimension may therefore be termed a lateral dimension. The second length dimension is the longest lateral dimension or a mean average value of the lateral dimensions of the particle, e.g. as measured along the length of the longitudinal dimension.

In certain embodiments the longitudinal dimension is 0.1 µm to 500 µm, e.g. 0.1 µm to 400 µm, 0.1 µm to 300 µm, 0.1 µm to 200 µm, 0.1 µm to 100 µm, 0.1 µm to 80 µm, 0.1 µm to 60 µm, 0.1 µm to 40 µm, 0.1 µm to 20 µm, 0.1 µm to 10 µm, 0.1 µm to 1 µm, 0.1 µm to 0.5 µm, 0.5 µm to 500 µm, 0.5 µm to 400 µm, 0.5 µm to 300 µm, 0.5 µm to 200 µm, 0.5 µm to 100 µm, 0.5 µm to 80 µm, 0.5 µm to 60 µm, 0.5 µm to 40 µm, 0.5 µm to 20 µm, 0.5 µm to 10 µm, 0.5 µm to 1 µm, 1 µm to 500 µm, 1 µm to 400 µm, 1 µm to 300 µm, 1 µm to 200 µm, 1 µm to 100 µm, 1 µm to 80 µm, 1 µm to 60 µm, 1 µm to 40 µm, 1 µm to 20 µm, 1 µm to 10 µm, 10 µm to 500 µm, 10 µm to 400 µm, 10 µm to 300 µm, 10 µm to 200 µm, 10 µm to 100 µm, 10 µm to 80 µm, 10 µm to 60 µm, 10 µm to 40 µm, 10 µm to 20 µm, 20 µm to 500 µm, 20 µm to 400 µm, 20 µm to 300 µm, 20 µm to 200 µm, 20 µm to 100 µm, 20 µm to 80 µm, 20 µm to 60 µm, 20 µm to 40 µm, 40 µm to 500 µm, 40 µm to 400 µm, 40 µm to 300 µm, 40 µm to 200 µm, 40 µm to 100 µm, 40 µm to 80 µm, 40 µm to 60 µm, 60 µm to 500 µm, 60 µm to 400 µm, 60 µm to 300 µm, 60 µm to 200 µm, 60 µm to 100 µm, 60 µm to 80 µm, 80 µm to 500 µm, 80 µm to 400 µm, 80 µm to 300 µm, 80 µm to 200 µm, 80 µm to 100 µm, 100 µm to 500 µm, 100 µm to 400 µm, 100 µm to 300 µm, 100 µm to 200 µm, 200 µm to 500 µm, 200 µm to 400 µm, 200 µm to 300 µm, 300 µm to 500 µm, 300 µm to 400 µm or 400 µm to 500 µm.

In certain embodiments the lateral dimension, or average thereof, is 0.01 µm to 20 µm, e.g. 0.01 µm to 16 µm, 0.01 µm to 12 µm, 0.01 µm to 8 µm, 0.01 µm to 4 µm, 0.01 µm to 2 µm, 0.01 µm to 1.6 µm, 0.01 µm to 1.2 µm, 0.01 µm to 0.8 µm, 0.01 µm to 0.4 µm, 0.01 µm to 0.2 µm, 0.01 µm to 0.1 µm, 0.01 µm to 0.05 µm, 0.05 µm to 20 µm, 0.05 µm to 16 µm, 0.05 µm to 12 µm, 0.05 µm to 8 µm, 0.05 µm to 4 µm, 0.05 µm to 2 µm, 0.05 µm to 1.6 µm, 0.05 µm to 1.2 µm, 0.05 µm to 0.8 µm, 0.05 µm to 0.4 µm, 0.05 µm to 0.2 µm, 0.05 µm to 0.1 µm, 0.1 µm to 20 µm, 0.1 µm to 16 µm, 0.1 µm to 12 µm, 0.1 µm to 8 µm, 0.1 µm to 4 µm, 0.1 µm to 2 µm, 0.1 µm to 1.6 µm, 0.1 µm to 1.2 µm, 0.1 µm to 0.8 µm, 0.1 µm to 0.4 µm, 0.1 µm to 0.2 µm, 0.2 µm to 20 µm, 0.2 µm to 16 µm, 0.2 µm to 12 µm, 0.2 µm to 8 µm, 0.2 µm to 4 µm, 0.2 µm to 2 µm, 0.2 µm to 1.6 µm, 0.2 µm to 1.2 µm, 0.2 µm to 0.8 µm, 0.2 µm to 0.4 µm, 0.4 µm to 20 µm, 0.4 µm to 16 µm, 0.4 µm to 12 µm, 0.4 µm to 8 µm, 0.4 µm to 4 µm, 0.4 µm to 2 µm, 0.4 µm to 1.6 µm, 0.4 µm to 1.2 µm, 0.4 µm to 0.8 µm, 0.8 µm to 20 µm, 0.8 µm to 16 µm, 0.8 µm to 12 µm, 0.8 µm to 8 µm, 0.8 µm to 4 µm, 0.8 µm to 2 µm, 0.8 µm to 1.6 µm, 0.8 µm to 1.2 µm, 1.2 µm to 20 µm, 1.2 µm to 16 µm, 1.2 µm to 12 µm, 1.2 µm to 8 µm, 1.2 µm to 4 µm, 1.2 µm to 2 µm, 1.2 µm to 1.6 µm, 1.6 µm to 20 µm, 1.6 µm to 16 µm, 1.6 µm to 12 µm, 1.6 µm to 8 µm, 1.6 µm to 4 µm, 1.6 µm to 2 µm, 2 µm to 20 µm, 2 µm to 16 µm, 2 µm to 12 µm, 2 µm to 8 µm, 2 µm to 4 µm, 4 µm to 20 µm, 4 µm to 16 µm, 4 µm to 12 µm or 4 µm to 8 µm.

Any and all combinations of longitudinal and lateral dimensions, and ranges thereof, disclosed above are specifically contemplated, in particular in combination with any and all aspect ratios, and ranges thereof. In view of the foregoing it may be seen that certain particles of use in the invention are rods, needles or fibres.

In view of the generality of the invention with regard to particle shape, in the context of particles which are not substantially, e.g. essentially, spherical, references to particle diameters are therefore references to equivalent spherical diameter. In these embodiments the particle has a shape defined by size dimensions that would result in the same size readings as a sphere of the same substance composition of said diameter in the particle size measuring technique used. In certain embodiments the size dimensions used are volume or surface area, preferably volume.

The mean (average) diameter, or equivalent spherical diameter, may be assessed by any convenient means, e.g. resistive pulse/Coulter method, sedimentation (gravity or centrifugation), optical imaging (e.g. SEM, static image analysis, dynamic image analysis), laser diffraction or light scattering, but for the purposes of the invention the Coulter method, in the form of Tunable Resistive Pulse Sensing, or optical means should be used to determine particle size.

ESM is the fibrous bilayer found in an egg between the albumen and the eggshell of avian eggs, e.g. the eggs of fowl (gamefowl/landfowl (Galliformes) and waterfowl (Anseriformes)) and poultry, in particular chicken, duck, goose, turkey, guineafowl, ostrich, pigeon, pheasant, partridge, grouse or gull. The eggs of *Gallus gallus domesticus*, the domestic chicken, are especially preferred. Either or both layers of the bilayer may be used in accordance with the invention.

The particle of use in the invention consists essentially of a micronized form of such a membrane. By "consists essentially of" it is meant that the particles contains at least 80% w/w micronized ESM, e.g. at least 85%, 90%, 91%, 92%, 93%, 94%, 95%, 96%, 97%, 98%, 99%, 99.5% or 99.9% w/w micronized ESM. In certain embodiments the particle consists of micronized ESM. In these embodiments moisture, i.e. water, is not included in the calculation of w/w, i.e. the calculation is based on components that are not water. However, the particle may still contain some moisture, e.g. up to 20%, 15%, 10%, 5% or 1% of the total mass of the particle may be contributed by water molecules. The individual particles of micronized ESM may have any shape, e.g. those described above. The shape of the micronized ESM may be the same or different to the shape of the particle of use in the invention. If a plurality of particles of micronized ESM are present, their shape may be essentially the same (i.e. the shape of the micronized ESM in the particle of use in the invention may be essentially homogenous) or may differ (heterogeneous). In certain embodiments the particles of micronized ESM in the particles of use in the invention are fibres, rods or needles.

To the extent permitted by the above definitions, the particle of use in the invention may further contain non-ESM substances, e.g. the excipients or further therapeutic agents disclosed herein. Preferably the particle is essentially free of other (non-ESM) egg components (which may be considered "contaminating" substances vis a vis ESM), e.g. albumen, yolk, and/or egg shell (calcium carbonate). By "essentially free" it is meant that the particle contains no more than 5% w/w, e.g. no more than 4%, 3%, 2%, 1%, 0.5%, 0.1%, 0.05% or 0.01% w/w of non-ESM egg components In certain embodiments the ESM component of the particle is a single micronized particle of ESM, in particular a fibre, rod or needle of micronized ESM.

It is believed that particles of micronized ESM with a high aspect ratio, e.g. fibres, rods or needles, and of the above described sizes (which may be interchangeably referred to herein as micro-fibres, micro-rods and micro-needles or nano-fibres, nano-rods and nano-needles depending on size) will have certain physical advantages over other forms of ESM (e.g. those of WO 2004/080428) at least in the context of the medical treatments described herein. In particular, such arrangements are believed to be able to provide ideal levels of surface area, turnover rates, wettability, moisture retention, spreadability and, in particular, MMP inhibition, especially in the context of wound healing and tissue engineering dressings/scaffolds.

In certain embodiments the particle of use in the invention is not substantially, e.g. essentially, spherical, i.e. is not a particle with an aspect ratio as defined above of less than 1.5, e.g. 1.4, 1.3, 1.2 or 1.1. In other embodiments the particle of use in the invention is not a sphere, i.e. is not a particle with an aspect ratio as defined above of 1.

In a further aspect there is provided a particle consisting essentially of micronized eggshell membrane (ESM), wherein said particle has a mean particle diameter of less than 100 µm.

The ESM of the particles of use in the invention may be separated from other egg components by any convenient means. The eggs from which the ESM may be separated may be fertilised or unfertilised. The eggs may be intact, i.e. prior to hatching, or may be empty, i.e. the remnants of the egg following hatching or following extraction of the egg contents (albumen and yolk). Suitable means are for example described in WO 2004/080428 and U.S. Pat. No. 8,580,315, the contents of which are incorporated herein by reference. Preferably the ESM is prepared by the method for harvesting eggshell membrane in-line in commercial egg processing plants disclosed in WO 2015/058790 (PCT/EP2013/072049) the contents of which are incorporated herein by reference. WO 2015/058790 provides a method of processing eggshell residues, which emanate from an egg breaking unit and comprise eggshell portions as well as membrane portions, comprising feeding eggshell residues (e.g. having a particle size of about 0.5 mm to about 40 mm and a wet basis moisture content of about 3% to about 40%) from the egg breaking unit into a cyclone driven by a process gas having a temperature of less than about 85° C. (preferably of less than about 60° C.) and having a speed exceeding about 60 m/s (preferably between about 70 m/s and about 340 m/s). Within said cyclone vortex processing of the eggshell residues reduces particle size and peels said membrane portions off of said eggshell portions, such that said eggshell portions become separated from said membrane portions. Through a top outlet of said cyclone there is released mainly a mix of process gas, vapour and droplets, and through a bottom outlet of said cyclone there is released mainly a mixture of separated eggshell portions and membrane portions. Said released mixture is then separated into an eggshell portion part and a membrane portion part in a sorting device. The resultant ESM portion may then be processed further into the ESM particles as described herein, preferably with no intervening steps.

In certain embodiments the method of preparing ESM comprises the further step of controlling time between feeding eggshell residues into and releasing said mixture out of said cyclone by adjusting an eggshell residue feed rate in relation to a total process gas feed rate, e.g. into an interval of about 0.5 s to about 20 s and preferably of about 1 s to about 5 s. In certain embodiments the method further comprises a step of centrifuging the eggshell residues prior to feeding them into said cyclone. In certain embodiments the feeding step is continuous. In other embodiments the sorting step comprises pneumatically expelling the membrane portion part off of sorting screens and out of the sorting device. The method may also comprise a final step of drying the membrane portion part.

ESM material in the form of flakes within the size range of around 1 $mm^2$ to about 10 $mm^2$ cannot be re-formed or processed into a sheet with the same characteristics as intact ESM. However, the current invention provides a means to present such material to the wound surface and promote wound healing.

In certain embodiments the ESM of the particle of use in the invention (or at least the protein components thereof) will be substantially that obtained from the shell-membrane separation process. In other words, the ESM of the particle of use in the invention will be substantially chemically unmodified as compared to naturally occurring ESM from a corresponding avian source.

More specifically the ESM of the particle of use in the invention will be chemically substantially non-degraded, non-digested (e.g. chemically or enzymatically) and/or non-denatured as compared to naturally occurring ESM from a corresponding avian source. By "substantially non-degraded" it is meant that less than 20%, e.g. less than 15%, 10%, 5% or 1% of the ESM components will show evidence of degradation as compared to naturally occurring ESM from a corresponding avian source. Non-digested and non-denatured should be interpreted accordingly. The degree of degradation/digestion/denaturation of ESM can be assessed by measuring the relative solubility of the ESM and/or the relative size or structure of the collagen fibres in the ESM. This may be achieved through routine techniques including immunohistochemistry/immunocytochemistry techniques and/or biomolecule (e.g. protein) stains and dyes.

In particular the ESM of the particle of use in the invention will not have been exposed to a hydrolysis reaction or a disulphide bond reducing reaction, e.g. chemical or enzymatic, in particular an alkaline hydrolysis reaction. In other words the ESM of the particle of use in the invention will be substantially non-hydrolysed, by which it is meant that less than 20%, e.g. less than 15%, 10%, 5% or 1% of the ESM components will show evidence of hydrolysis as compared to naturally occurring ESM from a corresponding avian source. The degree of hydrolysis of ESM can be assessed by measuring the relative solubility of the ESM and/or the relative size of the collagen fibres and/or the extent of collagen cross-linking in the ESM. This may be achieved through routine techniques including immunohistochemistry/immunocytochemistry techniques and/or protein stains and dyes.

In other embodiments the ESM of the particle of use in the invention will be substantially, e.g. essentially, insoluble in water at a neutral pH, e.g. pH 6.8-7.2. For the purposes of the invention an insoluble material requires greater than 10 L of solvent to dissolve 1 g of solute.

The ESM of the particle of use in the invention may be micronized by any convenient particle size reduction, micronizing, grinding, pulverizing or milling technology means, e.g. ball milling, bead milling, jet milling, vortex milling, followed by size selection, e.g. sieving and screening. The chosen particle size reduction method may be either performed dry or with a liquid medium. Cryo-pulverization may also be employed. In certain embodiments the particle size reduction process, and in certain embodiments the preceding ESM preparation process, is selected on the basis that ESM fibres of the required size (i.e. micro-fibres and nano-fibres) are produced. Inter alia, pulverisation of dry ESM in a rotating blade blender has been shown to be effective in this regard (FIG. 5).

In a further aspect the invention provides a method for the preparation of a micronized ESM containing particle as defined herein, said method comprising providing ESM, e.g. as defined herein, and subjecting the ESM to a micronization process and a particle size selection process. Preferably the ESM is provided essentially free of non-ESM egg components. More preferably providing ESM essentially free of non-ESM egg components comprises separating ESM from non-ESM egg components, e.g. as described in WO 2015/058790 (PCT/EP2013/072049) and above, and washing the ESM so obtained with a weak acid solution (which term includes a weakly acidic solution), e.g. an aqueous solution of about 0.1% hydrochloric acid or acetic acid, thereby removing any residual calcium carbonate in the ESM. In other embodiments the micronized ESM is washing with said weak acid solution. This weak acid wash, especially treatment with an about 0.1% HCl solution, not only demineralises the ESM, thus minimising the amount of inorganic salts in the ESM, but also removes and/or inactivates infective agents, e.g. microorganisms (e.g. as described herein), prions and viruses As shown in FIG. 5, micronization of ESM prepared in this way produces ESM fibres of 10-100 μm in length and a thickness of 1-5 μm (i.e. micro-fibres and nano-fibres).

Additional components of the micronized ESM containing particles of use in the invention may be included prior to the micronization process, during said process or after said process. The micronized ESM containing particles obtained or obtainable by said methods are a further aspect of the invention.

The particle of use in the invention will typically be provided as a part of a plurality of said particles, said plurality of particles having a mode particle diameter of less than 100 μm, e.g. less than 95, 90, 85, 80, 75, 70, 65, 60, 55, 50, 45, 40, 35, 30, 25, 20, 15, 10, 5, or 1 μm, e.g. less than 900, 850, 800, 750, 700, 650, 600, 550, 500, 450, 400, 350, 300, 250, 200, 150, 100, 50, 10, 5 or 1 nm.

In certain embodiments the plurality of particles also has a mode particle diameter of equal to or greater than 1 nm, e.g. equal to or greater than 5, 10, 50, 100, 150, 200, 250, 300, 350, 400, 450, 500, 550, 600, 650, 700, 750, 800, 850, 900 or 950 nm, or equal to or greater than 1 μm, e.g. equal to or greater than 5, 10, 15, 20, 25, 30, 35, 40, 45, 50, 55, 60, 65, 70, 75, 80, 85, 90 or 95 μm. Any and all range endpoints derivable from the combination of any of these values are specifically contemplated.

In certain embodiments less than 25%, e.g. less than 20%, 15%, 10%, 9%, 8%, 7%, 6%, 5%, 4%, 3%, 2%, 1%, 0.5% or 0.1% of the number of particles within said plurality of particles have a mean particle diameter equal to or greater than 100 μm.

In certain embodiments it may be advantageous to provide a plurality of particles with low dispersity. For this reason, the particles preferably have a coefficient of variation (CV) about the chosen mean particle diameter (as defined above) of less than 10%, more preferably less than 5%, still more preferably less than 2%. CV is determined in percentage as $$CV = 100 \times \text{standard deviation/mean}$$

where mean is the mean particle diameter and standard deviation is the standard deviation in particle diameter. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyser.

In other embodiments the plurality of particles are essentially monodisperse.

On the other hand, in certain other embodiments a broad range of particle sizes or a plurality of more narrow particle size ranges may be selected to achieve one or more of the various physiological effects described herein. Without wishing to be bound by theory, ESM particles of use in the invention having a mean particle diameter at the upper end of the size range may facilitate wound cell migration by providing a greater scaffolding effect whereas ESM particles of use in the invention having a mean particle diameter at the bottom end of the size range may have a greater inhibitory effect on MMPs and inflammation. It may be advantageous to select different size ranges in order to tailor the physiological effects of the ESM particles of use in the invention.

In further embodiments the particles of ESM used may be larger than described above, e.g. the particles may have a mean particle diameter of up to 500 μm, e.g. up to 450, 400, 300, 350, 200, 150, 125 μm, with any and all range endpoints derived from the combination of any of these values with previously recited values being specifically contemplated. The preceding discussion of the physical features of ESM particles and their production apply mutatis mutates to this part of the invention As discussed above, wounds are an ideal environment for infection, particularly chronic infection, due to their lack of an epithelial barrier and the availability of substrate and surface for microbial attachment and colonisation. Problematically, infection of a wound often delays healing, by increasing inflammation and necrosis in the wound and surrounding wound tissues, and thus renders that wound more susceptible to established (chronic) infection. Many wounds that struggle to heal comprise an infection and as such a wound healing treatment which may also deal with an infection in the wound (the so called bioburden of the wound) would be especially advantageous.

In certain embodiments the treatment of a wound with an ESM particle as defined herein in order to promote healing may also inhibit the viability and/or growth of a microorganism present in the wound and thereby combat a microbial infection present in the wound. Accordingly the invention can be considered to encompass a method to promote the healing of a wound in which the viability and/or growth of a microorganism present in the wound is also inhibited, or in which a microbial infection in the wound is also combated, wherein one or more ESM particles as defined herein are applied to said wound in an amount sufficient to inhibit the viability and/or growth of the microorganism, or to combat the microbial infection.

The term "microorganism" as used herein includes any cellular microbial organism, that is: any cellular organism that is microscopic, namely too small to be seen by the naked eye. In particular as used herein the term includes the organisms typically thought of as microorganisms, particularly bacteria, fungi, archaea, algae and protists. The microorganism may be prokaryotic or eukaryotic, and may be from any class, genus or species of microorganism. The microorganism may be aerobic or anaerobic. The microorganism may be pathogenic or non-pathogenic, or may be a spoilage or an indicator microorganism. The microorganism may be drug (i.e. antimicrobial drug, e.g. an antibiotic or an antifungal drug) resistant or multidrug resistant. In particular preferred embodiments the microorganism is capable of colonising a wound and delaying wound healing.

Bacteria or fungi represent preferred classes of microorganism and accordingly the ESM particles of use in the invention may be preferably viewed as having anti-bacterial or anti-fungal activity (e.g. bactericidal or bacteriostatic or fungicidal or fungistatic).

Preferably the bacteria are selected from the following genera: *Achromobacter, Acinetobacter, Actinobacillus, Aeromonas, Agrobacterium, Alcaligenes, Alteromonas, Bacteroides, Bartonella, Borrelia, Bordetella, Brucella, Burkholderia, Campylobacter, Cardiobacterium, Chlamydia, Chlamydophila, Chromobacterium, Chyseobacterium, Chryseomonas, Citrobacter, Clostridium, Comamonas, Corynebacterium, Coxiella, Cryptobacterium, Edwardsiella, Eikenella, Enterobacter, Enterococcus, Erwinia, Kingella, Klebsiella, Lactobacillus, Lactococcus, Legionella, Leptospira, Leptotrichia, Leuconostoc, Listeria, Listonella, Mobiluncus, Moraxella, Morganella, Mycobacterium, Mycoplasma, Neisseria, Nocardia, Nocardiopsis, Pantoea, Parachlamydia, Pasteurella, Peptococcus, Peptostreptococcus, Prevotella, Propionibacterium, Proteus, Providencia, Pseudomonas, Ralstonia, Rickettsia, Salmonella, Shewenella, Shigella, Sphingobacterium, Sphingomonas, Staphylococcus, Stenotrophomonas, Streptobacillus, Streptococcus, Streptomyces*, Treponem and *Yersinia*.

Thus, the bacteria may be Gram positive or Gram negative bacteria, or indeed Gram-indeterminate bacteria. Gram-negative bacteria are of importance. Within the Gram-negative bacteria the Enterobacteriaceae and the Gram-negative bacteria non-fermenting bacteria are of particular note.

Enterobacteriaceae include, but are not limited to, bacteria from the genera *Alishewanella, Alterococcus, Aquamonas, Aranicola, Azotivirga, Brenneria, Budvicia, Buttiauxella, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Phlomobacter, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia, Yokenella*. Preferred genera of Enterobacteriaceae include *Escherichia, Klebsiella, Salmonella, Shigella*, and *Yersinia* and *Providencia*.

Non-fermenting Gram-negative bacteria include, but are not limited to, bacteria from the genera *Pseudomonas, Acinetobacter, Stenotrophomonas* and *Burkholderia, Achromobacter, Algaligenes, Bordetella, Brevundimonas, Comamonas, Elizabethkingia* (formerly *Chryseobacterium*), *Methylobacterium, Moraxella, Ochrobactrum, Oligella, Psychrobacter, Ralstonia, Roseomonas, Shewanella, Sphingobacterium*, e.g. *Pseudomonas aeruginosa, Acinetobacter baumannii, Stenotrophomonas maltophilia*, and *Burkholderia* spp.

Preferably the bacteria may be selected from the genera *Pseudomonas, Acinetobacter, Burkholderia, Escherichia, Klebsiella, Streptococcus, Enterococcus, Providencia, Moraxalla, Staphylococcus*, e.g. *Pseudomonas aeruginosa, Acinetobacter baumannii, Burkholderia* spp, *E. coli, Klebsiella pneumoniae, Burkholderia cepacia, Burkholderia multivorans, Burkholderia mallei, Burkholderia pseudomallei, Acinetobacter lwoffii, Providencia stuartii, Providencia rettgeri, Providencia alcalifaciens, Klebsiella oxytoca, Pseudomonas anguilliseptica, Pseudomonas oryzihabitans, Pseudomonas plecoglossicida, Pseudomonas luteola, Moraxalla catarrhalis, Enterococcus faecium, Enterococcus faecalis, Streptococcus oralis, Staphylococcus aureus* (e.g. MRSA).

Thus, by way of representative example, the microorganism may be a bacteria of the genus *Staphylococcus, Pseudomonas, Legionella, Mycobacterium, Proteus, Klebsiella, Fusobacterium* or other enteric or coliform bacteria.

The microorganism may also be a, or from a, fungus, including for example fungi that may be, or may have been, classified as protista, e.g. fungi from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidioides brasiliensis, Blastomyces dermitidis, Pneomocystis carnii, Penicillium marneffi, Alternaria alternate*.

The microorganism may also be a protozoa, e.g. a member of the groups *Amoebae, Sporozoa, Ciliates*, and *Flagellates*. Representative protozoa include *Toxoplasma* species e.g. *Toxoplasma gondii, Plasmodium* species such as *Plasmodium falciparum, Plasmodium vivax, Plasmodium malariae. Trypanosoma* species e.g. *Trypanosoma brucei, Trypanosoma cruzi, Leishmania* species such as *Leishmania major*, and *Entamoeba* species such as *Entamoeba histolytica*.

Preferably the microorganism is selected from following genera: *Citrobacter, Enterobacter, Escherichia, Hafnia, Serratia, Yersinia, Peptostreptococcus, Bacteroides, Pseudomonas, Legionella, Staphylococcus, Enterococcus, Streptococcus, Klebsiella, Candida, Proteus, Burkholderia, Fusobacterium* and *Mycobacterium*, for instance, *Escherichia coli, Enterococcus faecalis Staphylococcus aureus, Staphylococcus epidermidis, Legionella pneumophila, Candida albicans, Pseudomonas aeruginosa, Burkholderia cepacia* and *Streptococcus pyogenes*. Infections caused by and *Pseudomonas*, e.g. *Pseudomonas aeruginosa*, infections are of particular note.

The microorganism may be in a biofilm, or put differently, the microorganism may be in a biofilm mode of growth. By "biofilm" it is meant a community of microorganisms characterized by a predominance of sessile cells that are attached to a substratum or interface or to each other (some motile cells may also be present) and that are embedded in a matrix of extracellular polymers (more specifically extracellular polymers that they have produced) characterised in that the microorganisms of this colony exhibit an altered phenotype with respect to growth rate and gene transcription (for example as compared to their "non-biofilm" or free-floating or planktonic counterparts). By "in a biofilm" it is meant that the microorganism is within (completely or in part), on or associated with the polymer matrix of a biofilm. Viewed differently, microorganisms that are "not in a biofilm" are microorganisms that are either in isolation, e.g. planktonic, or if in an aggregation of a plurality of microorganisms, that aggregation is unorganised and/or is devoid of the matrix characteristic of a biofilm. In each case, the individual microorganisms do not exhibit an altered phenotype that is observed in their biofilm dwelling counterparts.

The term "viability of a microorganism" means the ability of a microbe to survive under given conditions, e.g. in a wound. Survival can be considered equivalent to remaining alive. The ESM particles of use in the invention may reduce the viability of microorganisms through a microbicidal effect. Determining the viability of a microorganism can be done using the techniques detailed below for measuring microorganism cell death (and viability).

Thus, "inhibiting the viability" of a microorganism can include any effect which reduces the viability of a microorganism, or which renders it less likely to survive, or non-viable. In particular this term covers killing or destroying a microorganism.

The term "killing a microorganism" refers to the act of causing a microorganism to cease to be alive, i.e. to become dead. A microorganism is considered to be alive if it can be induced to replicate and/or grow, or at least display morphological changes, when placed in a medium that would normally support the growth of that microorganism and/or the microorganism is metabolising nutrients to release energy to support cellular functions. Typically, a microorganism can be considered to be dead if cell membrane integrity is lost.

Many routine assays are available to determine if a microorganism is alive (viable) or dead. One option is to place the microorganism in conditions that would normally support the growth of that microorganism and monitor the growth of the microorganism by appropriate standard means, e.g. by monitoring the size of the microorganism, the morphology of the microorganism, the number of microorganisms in the colony over time, the consumption of nutrients in the culture media, etc. Another option is to assess the microorganism for morphologies characteristic of cell death, e.g. necrotic or apoptotic bodies, membrane blebs, nuclear condensation and cleavage of DNA into regularly sized fragments, ruptured cell walls or membranes and leakage of cell contents into the extracellular environment. Other methods exploit the characteristic loss of cell membrane integrity in dead microorganisms. Membrane impermeable dyes (e.g. trypan blue and propidium iodide) are routinely used to assess membrane integrity. A still further option is to measure the metabolism of the microorganism. This can be done routinely in a number of ways. For instance the levels of ATP can be measured.

By "growth of a microorganism" it is meant both an increase in the size of the microorganism or in the amount and/or volume of the constituents of a microorganism (e.g. the amount of nucleic acid, the amount of protein, the number of nuclei, the numbers or size of organelles, the volume of cytoplasm) and an increase in the numbers of a microorganism i.e. an increase in the replication of a microorganism.

By "inhibiting the growth of a microorganism" it is meant that measurable growth (e.g. replication) of a microorganism, or the rate thereof, is reduced. Preferably measurable growth (e.g. replication) of a microorganism, or the rate thereof, is reduced by at least 50%, more preferably at least 60%, 70%, 80% or 90%, e.g. at least 95%. Preferably, measurable growth (e.g. replication) is ceased. Growth in terms of microbial size increase or expansion etc. may be inhibited independently of replication and vice versa. The ESM particles of use in the invention may inhibit the viability of microorganisms through a microbistatic effect and/or a microbicidal effect.

Thus, invention can also be seen to provide an ESM particle as defined herein for use in combating, and in particular in the treatment of, microbial infection in a wound, or the use of an ESM particle as described herein in the manufacture of a medicament for use in combating, and in particular in the treatment of, microbial infection in a wound. It will be seen in this aspect that the infection may be combated by inhibiting the growth and/or viability of a microorganism in a subject. The infection may be a biofilm infection.

"Combating an infection" can be viewed as the treatment or prevention of infection, e.g. including the prevention or inhibition of formation of an infection, the reduction or elimination of an infection, a reduction in the number of microbes in the colony making up the infection, a reduction or cessation in the rate of growth of the infection and/or the microorganisms therein, a reduction in or cessation of the rate of expansion in the number of microbes in an infection. "Combating biofilm" includes both preventative and reactionary measures or treatments. Combating biofilm therefore encompasses the prevention or inhibition of formation of a biofilm, the elimination or reduction of a biofilm, a reduction in biofilm size, a reduction in the number of microbes in a biofilm colony, a reduction or cessation in the rate of growth of a biofilm, a reduction in or cessation of the rate of expansion in the number of microbes in a biofilm colony, a reduction in the physical integrity of a biofilm, an increase in the sensitivity of the microbes in a biofilm colony to an anti-microbial agent or host immune defence mechanism and an increase in the permeability of a biofilm to an anti-microbial agent or host immune defence mechanism.

In these embodiments the microorganism will be contacted with the ESM particle of use in the invention following application of the particle to the wound. The term "contacting" encompasses applying the particle directly to the microorganism, or applying the particle to a wound to which the microorganism later comes into contact.

More particularly the microorganism will be contacted with an effective amount of the ESM particles of use in the invention, more particularly an amount of the ESM particles of use in the invention effective directly to inhibit the viability of (e.g. to kill) the microorganism or to inhibit directly the growth of the microorganism.

By "directly" it is meant that it is the ESM particles of use in the invention do not recruit physiological systems or mechanisms (e.g. the immune system) to impart their microbicidal or microbiostatic (e.g. their cytotoxic or cytostatic) effects. Rather, the ESM particles of use in the invention act directly on the microorganism.

In these embodiments a "sufficient (or effective) amount" of the ESM particles of use in the invention is that amount of ESM particles which results in the microbicidal or microbiostatic effects described above, or which effectively combats infection, and thereby promotes the healing of the wound. The skilled man would easily be able to determine what an effective (sufficient) amount of ESM particles would be on the basis of routine dose response protocols and, conveniently, the routine techniques for assessing microbial death or growth inhibition etc., as discussed above. The direct effects of the ESM particles of use in the invention can be assessed by using routine in vitro systems familiar to the skilled man which are devoid of complete physiological systems or mechanisms that may interfere with the assessment of microbicidal or microbiostatic effects (e.g. simple cell culture systems, isolated cell/virus systems, e.g. as disclosed in Example 1).

In one embodiment the method of the invention may comprise a step in which the subject will be diagnosed as having a wound that is also at risk of developing an infection or would benefit from having infection in it treated.

In a further embodiment, the method of the invention may comprise, following application of the ESM particles of use in the invention to the wound, a step in which the growth and/or viability of a microorganism in the wound or the extent of infection is monitored. These monitoring steps may involve comparison to the same metric immediately prior to application of the ESM particles of use in the invention to the wound or another point even earlier in the subject's treatment.

As discussed above, the normal wound healing process involves a proliferation stage in which the cells of the wound tissue migrate into the wound and/or proliferate to form de novo tissue, but in some instances the healing process becomes stuck in a preceding stage.

A wound healing treatment which may promote the viability and/or growth of the cells of the wound tissue would therefore be especially advantageous.

Thus, in certain embodiments the treatment of a wound with an ESM particle as defined herein in order to promote healing may also promote the viability and/or growth of the cells of the wound tissue. Accordingly, the invention can be considered to encompass a method to promote the healing of a wound in which the viability and/or growth of the cells of the wound tissue is also promoted, wherein an ESM particle as defined herein is applied to said wound in an amount sufficient to promote the viability and/or growth of the cells of the wound tissue.

The term "viability and/or growth" should be interpreted consistently with the above discussion in the context of microorganisms, although in this instance growth may also include differentiation of the cells of the wound tissue.

By "promoting the growth of the cells of the wound tissue" it is meant that measurable growth (e.g. replication and/or differentiation) of the cells of the wound tissue, or the rate thereof, is increased or at least maintained or prevented from decreasing. Preferably measurable growth (e.g. replication and/or differentiation) of the cells of the wound tissue, or the rate thereof, is increased by at least 5%, more preferably at least 10%, 20%, 30% or 40%, e.g. at least 50%.

In one embodiment the method of the invention may comprise a step in which the subject will be diagnosed as having a wound that would also benefit from having the viability and/or growth of the cells of the wound tissue promoted.

In a further embodiment, the method of the invention may comprise, following application of the ESM particles of use in the invention to the wound, a step in which the viability and/or growth of the cells of the wound tissue, and/or de novo tissue formation, is monitored. These monitoring steps may involve comparison to the same metric immediately prior to application of the ESM particles of use in the invention to the wound or another point even earlier in the subject's treatment.

A wound healing treatment which may also promote the migration of the cells of the wound tissue into the wound would therefore also be especially advantageous.

Thus, in certain embodiments the treatment of a wound with an ESM particle as defined herein in order to promote healing may also promote the migration of the cells of the wound tissue into the wound. Accordingly the invention can be considered to encompass a method to promote the healing of a wound in which the migration of the cells of the wound tissue into the wound is also promoted, wherein a ESM particle as defined herein is applied to said wound in an amount sufficient to promote the migration of the cells of the wound tissue into the wound.

By "promoting migration" it is meant that measurable migration of the cells of the wound tissue into the wound, or the rate thereof, is increased or at least maintained or prevented from decreasing. Preferably measurable migration of the cells of the wound tissue, or the rate thereof, is increased by at least 5%, more preferably at least 10%, 20%, 30% or 40%, e.g. at least 50%.

In one embodiment the method of the invention may comprise a step in which the subject will be diagnosed as having a wound that would also benefit from having the migration of the cells of the wound tissue into the wound promoted.

In a further embodiment, the method of the invention may comprise, following application of the ESM particles of use in the invention to the wound, a step in which the extent of the migration of the cells of the wound tissue into the wound, and/or de novo tissue formation, is monitored. These monitoring steps may involve comparison to the same metric immediately prior to application of the ESM particles of use in the invention to the wound or another point even earlier in the subject's treatment.

The promotion of migration and/or proliferation of wound cells may be due to the ESM particles of use in the invention acting as a scaffold for the cells of the wound tissue. The promotion of migration and/or proliferation may promote de novo tissue formation. The migration of the cells of the wound tissue into the wound, the role of the ESM particles in providing a scaffold and de novo tissue formation in the wound may be monitored and quantified by microscopic analysis of the wound or a sample thereof. Such analyses may involve chemical and/or immunochemical staining to detect molecular markers on the cells of the wound tissue and/or de novo tissue in the wound.

In these embodiments a "sufficient (or effective) amount" of the ESM particles as defined herein is that amount of ESM particles which results in the pro-proliferation or pro-migration effects described above, or which promotes de novo tissue formation, and thereby further promotes the healing of the wound. The skilled man would easily be able to determine what an effective (sufficient) amount of ESM particles would be on the basis of routine dose response protocols and, conveniently, the routine techniques for assessing wound cell viability, growth and migration discussed above.

In these embodiments the wound cells will be contacted with the ESM particle of use in the invention following application of the particle to the wound. More particularly the wound cells will be contacted with an effective amount of the ESM particles of use in the invention effective to promote the viability and/or growth of the cells of the wound tissue, promote the migration of the cells of the wound tissue into the wound or promote de novo tissue formation.

The micronized ESM containing particles of use in the invention have the additional benefit of being amenable to formulation in preparations that do not interfere with the maintenance of a moist healing environment. Thus, in the methods of the invention disclosed herein the ESM particles of use in the invention are applied to the wound so as not to interfere with the maintenance of a moist healing environment, e.g. in a formulation or dressing adapted so as not to interfere with the maintenance of a moist healing environment, e.g. those described herein.

In certain embodiments the methods of the invention achieve the promotion of wound healing with one or more, or all, of the above described additional wound effects, i.e. (i) the inhibition of the degradation of ECM and/or peptide growth or differentiation factors (in particular the inhibition of MMP activity against ECM and/or peptide growth or differentiation factors) and one or more, or all, of the above described additional wound effects, in particular the antimicrobial effect and/or the anti-inflammatory effects; and/or (ii) the reduction in inflammation in the wound and one or more, or all, of the above described additional wound effects, in particular the antimicrobial effect and/or the MMP inhibition effects.

The wound may be found in or on a subject. The term "in a subject" is used broadly herein to include sites or locations inside a subject or on a subject, e.g. an external body surface, and may include in particular a wound containing an implantable a medical device.

Thus, the wound may therefore be found in or on the skin or in or on any susceptible surface in the oral cavity (e.g. gingiva, gingival crevice, periodontal pocket), the reproductive tract (e.g. cervix, uterus, fallopian tubes), the peritoneum, the gastrointestinal tract, the ear, the eye, the prostate, the urinary tract, the vascular system, the respiratory tract, the heart, the kidney, the liver, the pancreas, the nervous system or the brain. The "cells of the wound tissue" should be interpreted accordingly. Preferably the wound is a skin (cutaneous) wound, in other words a dermal or dermatological wound, which includes wounds to any depth of the epidermis and/or dermis and the underlying tissue.

Implantable medical devices include, but are not limited to, any kind of percutaneous devices and/or line which results in a wound (e.g. central venous catheters, in particular catheters with cuffs, e.g. Dacron or collagen cuffs), prosthetic devices, e.g., heart valves, artificial joints, dental implants and soft tissue implants (e.g. breast, buttock and lip implants), stents, pacemakers, and tracheostomy tubes. An "implantable" medical device may include a device in which any part of it is contained within the body, i.e. the device may be wholly or partly implanted.

Wounds may be caused surgically, by physical injury (e.g. mechanical injuries; thermal injuries, for instance those resulting from excessive heat or cold; electrical injuries, for instance those caused by contact with sources of electrical potential; and radiation damage caused, for example, by prolonged, extensive exposure to infrared, ultraviolet or ionizing radiations) or by a spontaneously forming lesion such as a skin ulcer (e.g. a venous, diabetic or pressure ulcer), an anal fissure, a mouth ulcer and acne vulgaris. Surgically grafted tissue is considered to be a wound.

In the field of medicine, wounds are typically defined as either acute or chronic. Acute wounds are wounds that proceed orderly through the three recognised stages of the healing process following haemostasis (i.e. the inflammatory stage, the proliferative stage and the remodelling phase) without a protracted timecourse. Chronic wounds are defined as those which fail to heal or where there is excessive skin loss such as through burns. Such wounds do not complete the ordered sequence of biochemical events of the healing process because the wound becomes stalled in one of the healing stages. Commonly, chronic wounds are stalled in the inflammatory phase. Chronic wounds are a major source of morbidity for patients.

In accordance with a particular aspect of the present invention, a chronic wound may be considered to be a wound that has not healed in the expected amount of time, e.g. at least 5, 10, 15, 20 or 30 days longer than expected. The may be taken as a wound which has not healed at least 30, at least 40 days, particularly at least 50 days, more particularly at least 60 days, most particularly at least 70 days after formation.

Also of particular note are burn wounds which have become chronic. Any burn, in particular a severe burn, has a significant impact on the integrity of the epithelial and/or endothelial barrier of the subject and the healing of such traumas is often a lengthy process. As such, the methods of the invention may be considered to be methods for the promoting the healing of a chronic wound caused by a burn.

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

In certain embodiments the target wound is a wound also at risk of, or which contains, a microbial infection, e.g. those disclosed herein. The infection may be acute, or alternatively chronic, e.g. an infection that has persisted for at least 5 or at least 10 days, particularly at least 20 days, more particularly at least 30 days, most particularly at least 40 days.

In certain embodiments the target wound is a wound also at risk of, or which there is, inappropriate, i.e. insufficient, levels of wound tissue cell migration into the wound and/or proliferation or differentiation of wound tissue cells and/or de novo tissue formation.

In still further embodiments the target wound has (i) MMP overactivity (in particular against ECM and growth factors) or excessive ECM and growth factor degradation and one or more of the above described wound features, in particular microbial infection and inflammation; and/or (ii) excessive inflammation and one or more of the above described wound features, in particular microbial infection and MMP overactivity (in particular against ECM and growth factors) or excessive ECM and growth factor degradation.

In addition to the chronic wound healing effects of the micronized ESM-containing particles defined herein, it is expected that the sites of the surgical removal of a neoplasm would also benefit from treatment with ESM particles as defined herein as such treatments are predicted to be able to (i) combat neoplasm by inhibiting angiogenesis in any remnants of the neoplasm that remain following the surgical removal procedure and (ii) to prevent metastasis of any remnants of the neoplasm that remain following the surgical removal procedure by inhibiting MMP activity at the site of the surgical removal or ablation of a neoplasm.

Thus, the invention further provides a method for combating neoplasm or preventing metastasis of neoplasm, at a site at which a neoplasm, or a portion thereof, has been surgically removed, wherein one or more ESM particles as defined herein are applied to said site or the immediate vicinity of said site in an amount sufficient to combat any remnant neoplasm or prevent metastasis of the any remnant neoplasm.

In these embodiments the cells of any remnant neoplasm will be contacted with an ESM particle as defined herein following application of the particle to the site of surgical removal or its immediate vicinity. The term "contacting" encompasses applying the particle directly to the cells of any remnant neoplasm, or applying the particle to the site of surgical removal or its immediate vicinity and to which the cells of any remnant neoplasm later comes into contact. "Immediate vicinity" should be interpreted relative to the size of the neoplasm being removed. In some instances the immediate vicinity of the site of surgical removal or ablation will be an area that extends from the boundaries of the site of surgical removal by a distance that is up to 50%, e.g. up to 40, 30, 20, 10, 5 or 2%, of the widest part of the site.

"Combating neoplasm at a site at which a neoplasm has been surgically removed" can be viewed as the treatment of any remnants of the neoplasm that has been surgically removed in order to prevent, limit or inhibit the reformation of that neoplasm, the reduction or elimination of any remnants of the neoplasm, a reduction in the number of any remnant neoplastic cells at the site, a reduction or cessation in the rate of growth of any remnant neoplasm and/or any neoplastic cells therein or at the site, a reduction in or cessation of the rate of expansion in the number of neoplastic cells in the remnant neoplasm or at the site.

As mentioned, without wishing to be bound by theory, this combating effect is achieved, at least in part, by the prevention, inhibition, limitation or elimination of angiogenesis in any remnant neoplasm which in turn arises from the reduction or limitation in MMP activity against ECM proteins described herein. The detailed discussion of such effects applies mutatis mutandis to this part of the invention. Another mechanism may involve the obstruction of the growing blood vessels with the ESM particles themselves.

"Preventing metastasis of neoplasm at a site at which a neoplasm has been surgically removed" can be viewed as the treatment of any remnants of the neoplasm that has been surgically removed in order to prevent, limit or inhibit the metastasis of the cells of any such remnants. The treatment may prevent all metastasis events or may limit such events to an existing rate or probability or lower (inhibit) the rate or probability of metastasis.

As mentioned, without wishing to be bound by theory, this effect on metastasis is achieved by the reduction or limitation in MMP activity against ECM proteins described herein. The detailed discussion of such effects applies mutatis mutandis to this part of the invention.

This aspect of the invention can therefore be considered to encompass a method to prevent regrowth or recurrence of a neoplasm that has been removed from a subject surgically and/or a method to prevent relapse or recurrence of a subject's cancer and/or a method to improve the chances of remission following surgical removal of a neoplasm from a subject.

The neoplasm may be a neoplasm in any tissue of the subject's body, e.g. those tissues and body parts described herein. In certain embodiments the neoplasm is a malignant neoplasm, in particular a neoplasm with high metastatic potential or probability. The neoplasm may therefore be a sarcoma, carcioma, germinoma, lymphona, leukaemia, blastoma, papilloma and adenoma insofar as these neoplasms are characterised by a collection (mass) of cells. Such collections or masses may be described as "solid" even though the masses may be diffuse and/or comprise voids. In certain embodiments the tumour is a malignant or premalignant tumour, e.g. a sarcoma, carcinoma, germinoma, blastoma, lymphoma or leukaemia.

In more specific embodiments the neoplasm may be a colorectal tumour (also known as colon tumour, rectal tumour or bowel tumour), prostate tumour, testicular tumour, skin tumour (e.g. melanoma and non-melanoma (e.g. basal-cell tumour, squamous-cell tumour)), breast tumour, kidney (renal) tumour (e.g. Wilm's tumour), ovarian tumour, stomach (gastric) tumour, intestinal tumour (e.g. duodenal tumour, ileal tumour, jejunal tumour, small intestine tumour), liver (hepatic) tumour, pancreatic tumour, lung (pulmonary) tumour, oesophageal tumour, oral tumour, throat tumour, brain tumour (e.g. glioblastoma, medulloblastoma), adrenal tumour (e.g. adrenocortical tumour), thyroid tumour (e.g. anaplastic thyroid carcinoma), uterine tumour (e.g. uterine carcinosarcoma), haematological tumour (also known as the haematological malignancies) (e.g. haematopoietic and lymphoid tumour malignancies, e.g. leukaemia, lymphoma and myeloma).

In more specific embodiments the tumour may be a colorectal cancer (also known as colon cancer, rectal cancer or bowel cancer), prostate cancer, testicular cancer, skin cancer (e.g. melanoma and non-melanoma (e.g. basal-cell cancer, squamous-cell cancer)), breast cancer, kidney (renal) cancer (e.g. Wilm's tumour), ovarian cancer, stomach (gastric) cancer, intestinal cancer (e.g. duodenal cancer, ileal cancer, jejunal cancer, small intestine cancer), liver (hepatic) cancer, pancreatic cancer, lung (pulmonary) cancer, oesophageal cancer, oral cancer, throat cancer, brain cancer (e.g. glioblastoma, medulloblastoma), adrenal cancer (e.g. adrenocortical cancer), thyroid cancer (e.g. anaplastic thyroid carcinoma), uterine cancer (e.g. uterine carcinosarcoma), haematological cancer (also known as the haematological malignancies) (e.g. haematopoietic and lymphoid cancer malignancies, e.g. leukaemia, lymphoma and myeloma) or a non-malignant tumour in these anatomical sites (e.g. colorectal polyps, pilomatrixoma, hemangioma, osteoma, chondroma, lipoma, fibroma, lymphangioma, leiomyoma, rhabdomyoma, astrocytoma, meningioma, ganglioneuroma, papilloma, adenoma).

The manner of surgical removal is not limited and so may, for instance, be by excision or ablation, e.g. by mechanical, thermal or laser means, or cauterisation. Tumour ablation is a process by which a tumour, or a part or portion thereof, is destroyed by physical means and, typically, the remnants of the tumour resulting from the ablation step are left in situ. Surgical "removal" should therefore be construed accordingly. Representative tumour ablation methods include, but are not limited to cryoablation, hydrothermal ablation, ionising radiation ablation (external beam radiation therapy or brachytherapy), radioablation, ultrasound ablation, laser ablation, microwave ablation and electroablation. Such methods are well practiced in the field of cancer therapy.

The subject may be any human or non-human animal subject, but more particularly may be a human or non-human vertebrate, e.g. a non-human animal selected from mammals, birds, amphibians, fish and reptiles. Mammalian subjects are preferred. The non-human animal may be a livestock or a domestic animal or an animal of commercial value, including laboratory animals or an animal in a zoo or game park. Representative non-human animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, tilapia, catfish, bream, barramundi, grouper, mullet, amberjack, croaker, rohu, goby, cod, haddock, sea bass and carp. Veterinary uses of the invention are thus covered. The subject may be viewed as a patient. Preferably the subject is a human.

"Treatment" when used in relation to the treatment of a medical condition (e.g. a wound) or infection in a subject in accordance with the invention is used broadly herein to include any therapeutic effect, i.e. any beneficial effect on the condition or in relation to the infection. Thus, not only included is eradication or elimination of the condition/ infection, or cure of the subject of the condition/infection, but also an improvement in the infection/condition of the subject. Thus included for example, is an improvement in any symptom or sign of the infection/condition, or in any clinically accepted indicator of the infection/condition (for example a decrease in wound size (depth and/or area), an acceleration of healing time, one or more of the wound effects described herein, or a reduction in general discomfort or pain in the wound or surrounding tissue). Treatment thus includes both curative and palliative therapy, e.g. of a pre-existing or diagnosed infection/condition, i.e. a reactionary treatment.

"Prevention" as used herein refers to any prophylactic or preventative effect. It thus includes delaying, limiting, reducing or preventing the condition (e.g. an increase in the size of the wound or the development of a chronic or poorly healing wound) or infection or the onset of the condition/infection, or one or more symptoms or indications thereof, for example relative to the condition/infection or symptom or indication prior to the prophylactic treatment. Prophylaxis thus explicitly includes both absolute prevention of occurrence or development of the condition/infection, or symptom or indication thereof, and any delay in the onset or development of the condition/infection or symptom or indication, or reduction or limitation on the development or progression of the condition/infection or symptom or indication.

Specifically, the micronized ESM containing particles as defined herein can be taken as a prophylactic treatment, for example to prevent, or at least minimise the risk of, wound infection or to prevent, or at least minimise the risk of, an increase in wound size or development of a poorly healing or chronic wound.

A "pharmaceutically effective" or "physiologically effective" amount of the micronized ESM containing particles of use in the invention is the amount of particles that measurably promotes the healing of a target wound. More specifically, this may be the above described amounts sufficient to (effective to) achieve the various physiological effects described above.

Suitable doses of the micronized ESM containing particles of use in the invention which may achieve the pharmaceutically/physiologically effective amounts will vary from subject to subject and can be determined by the physician or veterinary practitioner in accordance with the weight, age and sex of the subject, the severity of the condition/infection, the mode of administration and also the particular ESM particle selected.

By "applied to the wound" it is meant that the micronized ESM containing particles of use in the invention are not administered to the subject systemically with a view to having the ESM particles reaching the wound predominantly via the blood or lymph circulation of the subject, i.e. the micronized ESM containing particles of use in the invention are brought into contact with the wound from a point which is not the blood or lymph circulation of the subject. This may be considered a local or topical application. Typically micronized ESM containing particles of use in the invention are applied directly to the surface and/or interior of the wound.

The micronized ESM containing particles of use in the invention may be applied (administered) to the wound to in any convenient topical form. At its most simple the particles may be applied as a dry powder without further formulation. The dry powder formulation may be applied to the wound surface by sprinkling the powder so as to cover the wound surface to a layer of, for instance, 0.5 mm or less. ESM does not have intrinsic moisture absorbance capacity so it may be beneficial in certain embodiments to place an additional wound dressing, e.g. those of the types discussed below, on top of the powder treated wound. For dry wounds where debridement is indicated, it may be beneficial to treat the wound surface with a soft or liquid/fluid gel formulation (e.g. a hydrogel or a soft hydrocolloid gel) and then apply the dry particles of ESM on top of the gel.

The skilled man will, however, also be able to formulate the micronized ESM containing particles of use in the invention into pharmaceutical compositions that are adapted for topical administration according to any of the conventional methods known in the art and widely described in the literature.

The ESM particles of use in the invention may be incorporated, optionally together with other active agents, with one or more conventional carriers, diluents and/or excipients, to produce conventional topical preparations such as powders, beads sachets, suspensions, emulsions, solutions, aerosols (as a solid or in a liquid medium), sprays (e.g. nasal sprays), ointments, salves, creams, pastes, films, gels (e.g. hydrogels and hydrocolloids), foams and so on. Merely for guidance only, Example 5 describes the production of a hydrocolloid ESM particle gel. Such gels would be expected to hydrate the wound to which they are applied, allow aqueous debridement and bring the ESM benefits discussed above. Such compositions are suited to use in dry necrotic wounds. Examples 6 to 9 provide further specific embodiments.

The present invention therefore also provides a pharmaceutical composition, e.g. for use in any of the above-mentioned methods or medical treatments of the invention, comprising a micronized ESM-containing particle as defined herein together with at least one pharmaceutically acceptable carrier, diluent or excipient.

Examples of suitable carriers, excipients, and diluents are lactose, dextrose, sucrose, sorbitol, mannitol, starches, gum acacia, calcium phosphate, inert alginates, tragacanth, gelatin, pectin, fibronectin, elastin, calcium silicate, microcrystalline cellulose, polyvinylpyrrolidone, cellulose (e.g. oxidised regenerated cellulose, methyl cellulose carboxymethylcellulose, hydroxyethylcellulose), water syrup, water, water/ethanol, water/glycol, water/polyethylene, hypertonic salt water, glycol, propylene glycol, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents and the like. Monovalent, divalent or trivalent metal cation alginates, in particular sodium, calcium, zinc and silver alginates are of note.

The micronized ESM-containing particles of use in the invention can also be incorporated into wound dressings e.g. woven and non-woven dry fibrous (e.g. fabric) dressings, film-based dressings, gel-based dressings or dressings which are a combination of these dressings types. The micronized ESM-containing particles of use in the invention may be applied to the dressing prior to or during application to a wound or may be incorporated during manufacture. The dressings will typically be adapted or used such that the micronized ESM-containing particles of use in the invention will be exposed to the wound or wound fluid when in use.

Fibrous dressings of use in the invention may include cotton, alginate, cellulose (e.g. oxidised regenerated cellulose, carboxymethylcellulose, hydroxyethylcellulose), fibrous collagen, and ESM (U.S. Pat. No. 7,767,297, incorporated herein by reference) based dressings.

Film-based dressings are typically semi- or impermeable to water and flexible and may be formed from any suitable plastic, e.g. polyurethane, polyvinylchloride.

Gel-based dressings, which include hydrogels and hydrocolloid gels, may be formed from a plethora of polymeric substances, including, but limited to, alginate, cellulose (e.g. oxidised regenerated cellulose, methylcellulose, carboxymethylcellulose, hydroxyethylcellulose), collagen, pectin, elastin, fibronectin. The inclusion of biopolymers, gums or resins (e.g. gelatin) can help ensure that the dressing adheres lightly to the wound surface. The inclusion of alginate may increase the moisture capacity of the gel matrix. Such basic alginate gels for wound healing are described in U.S. Pat. No. 6,201,164.

Gel-based dressings may be suited for wounds with a deep cavity or which may be tunneled beneath healthy skin. In the latter type of wound, the gel may be loaded into a syringe and then delivered to the cavity to ensure that all wound surfaces are covered. When in use, it may be beneficial to cover gel-based dressings with a secondary dressing, e.g. a fibrous dressing and/or a film dressing in order to maintain placement of the gel and/or retain moisture in the gel and wound and/or to act as a barrier to microbes. A gel-based dressing of the invention may be designed to have such a secondary element integral to the gel element.

Further topical systems that are envisaged to be suitable are in situ drug delivery systems, for example gels where solid, semi-solid, amorphous or liquid crystalline gel matrices are formed in situ and which may comprise the micronized ESM-containing particles of use in the invention. Such matrices can conveniently be designed to control the release of the particles from the matrix, e.g. release can be delayed and/or sustained over a chosen period of time. Such systems may form gels only upon contact with biological tissues or fluids. Typically the gels are bioadhesive. Delivery to any body site that can retain or be adapted to retain the pre-gel composition can be targeted by such a delivery technique. Such systems are described in WO 2005/023176.

Hydrocolloid gels used in the management of wounds may be supplied as either soft or fluid/liquid gels or firm and solid gels. Examples of firm hydrocolloid gels are sold under the brand names of Granuflex® and Duoderm® They have moderate fluid absorbency and maintain a moist wound bed without inducing maceration to the wound bed and surrounding skin. In response to wetting, they swell and remain viscous and retain the absorbed fluid. Soft or fluid/liquid hydrogels suitable for use in wounds have been described in the art, such as in U.S. Pat. No. 5,503,847.

In a further specific embodiment, the invention further provides a wound dressing, preferably a hydrocolloid or hydrogel dressing, comprising a micronized ESM-containing particle as defined herein e.g. for use, where appropriate, in the methods and medical treatments of the invention.

In a preferred embodiment the carrier system selected may also enhance the wound healing process separately to the contribution of the ESM component.

In one example, a functional hydrocolloid gel wound dressing incorporating micronized ESM-containing particles of use in the invention can be manufactured from pectin, sodium carboxymethyl cellulose and propylene glycol, e.g. wherein the pectin is present at 0.05% and 1% by weight, CMC is present at 2% and 4.5% by weight, propylene glycol is present between 15-20% by weight and the ESM particles are present at 0.5% and 10% by weight, with water making up the remainder to 100% by weight. In this embodiment, the formulation is additionally capable of cleansing and debriding the wound and absorbing moderate quantities of exudate. These functions augment the activity of micronized ESM-containing particles which is believed to bind and deflect proteases from wound bed destruction and acts as a scaffold to allow cellular attachment and migration through the wound bed. This hydrocolloid formulation is ideally suited for wounds with a deep cavity or which may be tunneled beneath healthy skin. In the latter type of wound, the gel may be loaded into a syringe and then delivered to the cavity to ensure that all wound surfaces are covered.

In a further embodiment micronized ESM-containing particles of use in the invention may be formulated in a substantially pure water/hydroxyethylcellulose hydrogel. Such a formulation may be prepared by dissolving HEC in water with agitation or stirring and dispersing ESM within said aqueous HEC solution. The ESM-HEC hydrogel may then be packaged into convenient receptacles, e.g. into tubes, and then the filled receptacles may be sterilised with gamma radiation at, e.g., 25 kGy.

Solid or firm gel hydrocolloids may also be manufactured which incorporate a semi-permeable backing sheet which may act as a sterile barrier as well as functioning in management of moisture within the wound surface. Such solid materials may incorporate polymers or gums or resins or gelatin to ensure that the dressing adheres lightly to the wound surface. Such products would be suited to the treatment of lightly to moderately exuding non-cavity wounds. Such dressings would not require a secondary dressing to keep them in place or to provide an anti-microbial barrier.

Optionally, the hydrocolloid gel may contain alginate to increase the moisture capacity of the base matrix gel. This would be preferable in wounds with moderate to high exudate. Such basic alginate gels are described in U.S. Pat. No. 6,201,164.

As is clear from the foregoing, alginate-based wound dressings, e.g. fibrous or gel, dry, substantially dry or moist, are notable delivery systems for the micronized ESM-containing particles of use in the invention. Alginate-based dressings represent a flexible and adaptable technology which may permit ESM particles to the delivered to a wound in a number of different ways and formats. Of particular note are ESM-alginate composite dressings in which ESM particles of use in the invention are combined with alginate and wound dressings, or elements thereof, are manufactured from that composite mixture or formed in situ. Such dressings are particularly useful in management of wounds with a high exudate. The composite dressings maintain an advantageous moisture level in the wound bed, absorbing excess exudate whilst facilitating ESM contact with the regenerating tissues. Such dressings or the ESM-alginate composite containing elements thereof may be provided in dry, substantially dry or moist forms which are capable of absorbing wound fluid.

ESM-alginate composite dressings are made possible because alginate has the ability to from a cross-linked gel in the presence of sufficient amounts of divalent or trivalent metal cations (e.g. $Ca^{2+}$, $Be^{2+}$, $Mg^{2+}$, $Sr^{2+}$, $Ba^{2+}$, $Fe^{2+}$, $Fe^{3+}$ $Al^{3+}$ or $Zn^{2+}$), but in the absence of sufficient amounts of di- or trivalent metal cations or the presence of monovalent metal cations (e.g. $Na^+$, $Li^+$, $K^+$, $Rb^+$ or $Cs^+$) alginate is essentially soluble in aqueous solutions, albeit with high water retention properties and the ability to form a non-cross linked gel. At its simplest, ESM may be mixed with a fluid alginate solution and then cross-linking or precipitation may be initiated subsequently e.g. in the wound itself upon contact with $Ca^{2+}$ in the wound.

Di- or trivalent metal ion-alginate gels have varying material properties which are determined, inter alia, by the moisture absorbency of the material, which in turn is determined by the degree of di- or trivalent metal ion substitution. Thus, by varying the ratio of di- or trivalent to monovalent metal ions (e.g. $Ca^{2+}$ and $Na^+$) in alginate containing mixtures one can prepare a spectrum of gels with a wide range of properties. By removing moisture from such gels prior to use one can prepare dry forms, including fibres, with significant moisture absorbency when in use. Advantageously absorbent alginate dressings may be based on mixtures of di- or trivalent metal ion alginate and monovalent metal ion alginate. The di- or trivalent metal ion alginate contributes to structural strength of the dressing and monovalent metal ion alginate promotes absorbance. A balance must be struck as an excess of di- or trivalent metal ion alginate will result in a dressing that cannot be returned to a flexible gel form by physiological solutions found at wound sites due to an inability to counter the concentration of di- or trivalent metal ion in the material. An excess of monovalent metal ion alginate, will result in decreased strength and poorer handling properties, particularly fibre qualities. Nevertheless, composite mixtures of monovalent metal ion alginates and ESM particles may prove useful because exposure to $Ca^{2+}$ can occur in situ and thus lead to in situ cross-linked gel formation, i.e. formation of a dressing in situ.

As described in Examples 6 to 9 the addition of ESM particles of use in the invention to solutions of monovalent metal ion alginate (sodium alginate) and subsequent gelation of that mixture with a $Ca^{2+}$ solution ($CaCl_2$) or $Ca^{2+}$ from the wound itself can form the basis of ESM-alginate composite dressings, e.g. in the form of granules, gel pads and fibres. Such forms may be dried to lower the moisture content, thereby enhancing absorbency when in use and shelf-life and facilitating transport and storage. Many other structural forms would be apparent to the skilled person and may be prepared without undue burden, e.g. powders may be formed through spray drying or spraying solutions of ESM particles and monovalent metal ion alginate into di- or trivalent metal ion solutions. A review of the preparation of alginate fibres is Qin, Y., 2008, Polymer International, 57:171-180, the contents of which are incorporated herein by reference. The ESM particles of use in the invention may therefore be included in calcium, sodium, calcium-sodium, zinc and silver alginate and alginic acid fibres, e.g. as described in Qin.

Thus, in a further specific embodiment, the invention further provides a wound dressing, or a structural element thereof, comprising (e.g. formed from) a composite mixture of an micronized ESM-containing particle as defined herein and an alginate. The dressing may be provided for use, where appropriate, in the methods and medical treatments of the invention.

References to alginate include alginic acid unless context dictates otherwise. The alginate of the dressing may be alginic acid, a divalent metal ion alginate, trivalent metal ion alginate and/or a monovalent metal ion alginate, e.g. those recited above, in particular $Ca^{2+}$ and/or $Na^+$ alginate, respectively. Preferably the composite mixture of a micronized ESM-containing particle as defined herein and the alginate of the wound dressing is a gel, e.g. a cross-linked gel, including fibres, pads, granules and powders formed from such gels. The alginate will typically be a polymer, e.g. of at least 35 kDa, or plurality of polymers of different sizes, although smaller oligomers may be used in place of said polymers or in combination with said polymers.

The composite mixture of a micronized ESM-containing particle as defined herein and the alginate of the wound dressing may be dry (less than 2% moisture by weight as measured by the loss on drying test method), substantially dry (less than 5% moisture by weight) or moist (greater than 5% moisture by weight).

The composite mixture of a micronized ESM-containing particle as defined herein and the alginate of the wound dressing may alternatively be in the form of a powder, granules, a macroscale solid support (e.g. a pad or sponge) or a fibre. The wound dressing may consist essentially of one or more of said powder, granules, macroscale solid support, or fibre. In other embodiments the wound dressing may comprise at least a second structural element, e.g. a structural element formed from the films, fibres and gels described above in the context of film-, fibre- or gel-based dressings. An impermeable backing may be of note.

Additional gel rheology modifying materials, e.g. carboxymethylcellulose, hydroxyethylcellulose, methylcellulose or pectin may be incorporated into composite mixtures, e.g. to further modify the moisture retention properties of the composite and/or the mechanical properties of the composite.

The micronized ESM containing particles of use in the invention can also be incorporated into or onto implantable medical devices and thus application to the wound may be achieved in this way also. Such medical devices may be those described herein including but not limited to, any kind of percutaneous devices and/or line which results in a wound (e.g. central venous catheters, in particular catheters with cuffs, e.g. Dacron or collagen cuffs), prosthetic devices, e.g., heart valves, artificial joints, dental implants and artificial soft tissue implants (e.g. breast, buttock and lip implants), stents, pacemakers, and tracheostomy tubes.

The clinical usefulness of catheters, for example haemodialysis catheters, is limited where these become infected (Wayne et al 2005; J Am Soc Nephrol 16: 1453-1462). Exit sites may be treated with antibiotics to reduce bacterial growth but such use is often associated with the development of antibiotic resistance. In many cases, once an exit site is chronically infected, the catheter must be removed. The micronized ESM containing particles as defined herein, by promoting wound repair and tissue growth around the exit site as well as inhibiting the growth of bacteria, would prolong the infection-free useful clinical life of a catheter, for example. Tissue in-growth onto the exterior of a catheter which has been coated with micronized ESM-containing particles as defined herein would effectively seal the path for potential infection through the exit site.

Thus, in a further aspect the invention provides an implantable medical device whose susceptible surfaces, or a portion thereof, e.g. percutaneous cuff, have been pretreated with a micronized ESM-containing particle as defined herein.

By "pretreated" it is meant that the susceptible surface is exposed to a micronized ESM-containing particle as defined herein prior to implantation in a subject in such a way that the particle persists on the surface for a duration sufficient to promote wound healing or any or the wound effects described herein for an appreciable duration of time. Preferably the particle will persist for substantially the useful life of the surface, e.g. the pretreatment results in a substantially permanent coating of a micronized ESM-containing particle as defined herein. Thus a pre-treated surface/device is one to which a micronized ESM-containing particle as defined herein is applied and on which it remains. Such a device/ surface may be a coated and/or impregnated device/surface. Preferably a coating will comprise a plurality, i.e. at least two, layers of ESM particles.

Pretreatment can be achieved by any convenient means, for example any form of applying a micronized ESM-containing particle as defined herein to the surface, notably coating the surface, e.g. spray drying, polymer coating with a polymer incorporating the a micronized ESM-containing particle as defined herein, or disposing a firm hydrogel or hydrocolloid on the surface. Coating may occur immediately prior to or during implantation. Such a "coating" composition containing an micronized ESM-containing particle as defined herein is a further aspect of the present invention. Alternatively, the micronized ESM-containing particle as defined herein can be incorporated or impregnated into the material from which the device or its susceptible parts are manufactured. This approach is suited to devices, or constituent parts thereof, manufactured from polymers such as plastics and silicones. Implantable medical devices comprising an inanimate surface comprising a micronized ESM-containing particle coating or coating composition, or incorporating, or impregnated with, an micronized ESM-containing particle as defined herein are therefore contemplated.

The present invention also provides for the use of a micronized ESM-containing particle as defined herein to prepare or manufacture a composition, wound dressing or implantable device comprising a micronized ESM-containing particle as defined herein.

The micronized ESM-containing particles proposed for use according to the invention may be used in combination with other therapeutic agents, for example to be administered together, in a single pharmaceutical formulation or composition or dressing or device (e.g. those described herein), or separately (i.e. for separate, sequential or simultaneous administration). Thus, the micronized ESM-containing particles of use in the invention may be combined with a second (or further) therapeutically active agent, e.g. in a pharmaceutical kit or as a combined ("combination") product. The further therapeutic agent may be administered by any convenient means and so not necessarily topical means, e.g. parenteral or enteral (for instance oral, intravenous or by inhalation). The agents may be used separately, or together in the same composition or dressing or device, simultaneously or sequentially or separately, e.g. at any desired time interval.

In one advantageous embodiment of the invention the micronized ESM-containing particles as defined herein may be used in the methods of the invention in conjunction or combination with a second or further clinically-useful anti-microbial agent (hereinafter "further anti-microbial agent"). The agents may be used separately, or together in the same composition or dressing or device, simultaneously or sequentially or separately, e.g. at any desired time interval.

Thus, by way of representative example, the further anti-microbial agent may be used after the particles are applied to the wound, but a preceding or simultaneous use may be beneficial in some circumstances.

Representative antibiotics include, but are not limited to the aminoglycosides (e.g. amikacin, gentamicin, kanamycin, neomycin, netilmicin, streptomycin, tobramycin); the carbecephems (e.g. loracarbef); the 1st generation cephalosporins (eg cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the carbapenems (e.g. imipenem, meropenem, ertapenem, doripenem, panipenem/betamipron, biapenem, PZ-601); chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

Representative antiseptics include, but are not limited to chlorine bleach (sodium hypochlorite), quaternary ammonium compounds (e.g. benzalkonium chloride, cetyl trimethylammonium bromide, cetylpyridinium chloride), hydrogen peroxide, phenol compounds (e.g. TCP Triclosan), alcohols (e.g. ethanol), Virkon™, iodine compounds (e.g. povidone-iodine), silver compounds (e.g. elemental silver nano/microparticles).

Antimicrobial surfactants are another class of antiseptics. These are compounds that disrupt microbial cell membranes and other structural components and therefore inhibit growth and/or viability of microorganisms. Antimicrobial surfactants and their use in antimicrobial compositions is well known in the art should further guidance be needed the discussion of antimicrobial surfactants in "Preservative-free and self-preserving cosmetics and drugs—Principles and practice", Ed. Kabara and Orth, Marcel Dekker, NY, NY, 1997, is explicitly incorporated by reference in its entirety. Antimicrobial surfactants may be anionic, cationic, nonionic or amphoteric. Examples of antimicrobial anionic surfactants include, but are not limited to, sodium dodecyl sulfate (sodium lauryl sulfate), sodium dodecyl aminopropionic acid, sodium ricinoleate, bile acids, alkylaryl sulfonates, Grillosan DS7911, disodium undecylenic acid monoethanol amidosulfosuccinate. Examples of antimicrobial cationic surfactants include, but are not limited to, the quaternary ammionium compounds, the aminimides and chlorhexidine compounds. Examples of antimicrobial nonionic surfactants include, but are not limited to, the monoesters of fatty acids, polyethyleneglycomonoesters of alkyldihydroxybenzoic acids, glucosamine derivatives and diethanolamides of N-lauroyl dipeptides. Examples of antimicrobial amphoteric surfactants include, but are not limited to, the alkyl betaines, the alkylamidopropylbetaines, the alkyl aminopropionates, the alkyliminodipropionates and the alkylimidazolines.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine The further anti-microbial agent may conveniently be applied before, simultaneously with or following the micronized ESM-containing particles of use in the invention. Conveniently the further anti-microbial agent is applied at substantially the same time as the ESM particles or afterwards. For example, the further anti-microbial agent is applied at least 1 hour, preferably at least 3 hours, more preferably at least 5 and most preferably at least 6 hours after the ESM particles are administered. In other embodiments the further antimicrobial may conveniently be applied or administered before the ESM particles, e.g. at least 1 hour, at least 3 hours, at least 6 hours before the ESM particles. In these embodiments the ESM particles can be applied or administered with or without a further application of the further antimicrobial. To optimise the anti-microbial effect of the further anti-microbial agent it can be given (e.g. administered or delivered) repeatedly at time points appropriate for the agent used. The skilled person is able to devise a suitable dosage or usage regimen. In long term treatments the ESM particles can also be used repeatedly. This can be as frequently as the further anti-microbial agent, but may be less frequently. The frequency required will depend on the colony composition, the anti-microbial used and its route of administration and the skilled person is able to optimise the dosage or usage patterns to optimise results.

The use of the micronized ESM containing particles defined herein in combination or conjunction with a growth factor, e.g. PDGF, FGF, EGF, TGF, hGF may also be beneficial. Suitable treatment regimens may be as described in the context of the use of a further antimicrobial agent.

The use of the micronized ESM containing particles defined herein in combination or conjunction with an anti-inflammatory agent, e.g. an anti-inflammatory steroid or an NSAID, may be beneficial. Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen naproxen, oxaprozin), the acetic acid derivatives (e.g. aceclofenac, diclofenac, etodolac., indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen naproxen, oxaprozin) are preferred, ibuprofen being most preferred. Suitable treatment regimens may be as described in the context of the use of a further antimicrobial agent.

The invention will be further described with reference to the following non-limiting Examples in which:

FIG. 1 shows bacterial growth curves for *Escherichia coli* in the absence of or presence of ESM particles with a mean particle diameter of 100 μm (0.003 g or 0.01 g added ESM particles). The lower two traces are ESM added.

FIG. 2 shows the effect of ESM particles with a mean particle diameter of less than 100 μm on the inflammatory response of U937 human monocyte cells containing an NF-kB-controlled luciferase reporter construct to LPS as measured by NF-kB-activity. Control=no ESM added. Non-LPS: left hand bar; LPS: right hand bar.

FIG. 3 shows the effect of ESM particles with a mean particle diameter of less than 100 μm on the activity of recombinant MMP-9. Without MMP9: left hand bar; With MMP9: right hand bar.

FIG. 4 shows the effect of MMP inhibitor GM6001 on MMP-9 activity in the same assay as that used to produce the results displayed in FIG. 3.

FIG. 5 shows ESM fibres formed from the pulverization of dry ESM flakes in a rotating blade blender, said dry ESM flakes having been prepared by separating ESM from non-ESM egg components as described in WO 2015/058790 (PCT/EP2013/072049) and above, washing the ESM flakes so obtained with 0.1% hydrochloric acid, thereby removing any residual calcium carbonate in the ESM flakes, and drying the ESM flakes.

FIG. 6 shows the effect of four different formulations of ESM particles on the closure of full-thickness excisional wounds in the db/db diabetic mouse as measured by percentage wound area remaining following treatment. The four ESM formulations are described in Example 10. Data from these treatments are plotted against those from a 'no treatment' group (negative control) and a positive control group (treatment with platelet-derived growth factor-BB (rh-PDGF-BB [10 μg]) and transforming Growth Factor-alpha (rh-TGF-α [1 μg]) in 0.5% HPMC (Hydroxypropyl methyl cellulose))

Figure 12:
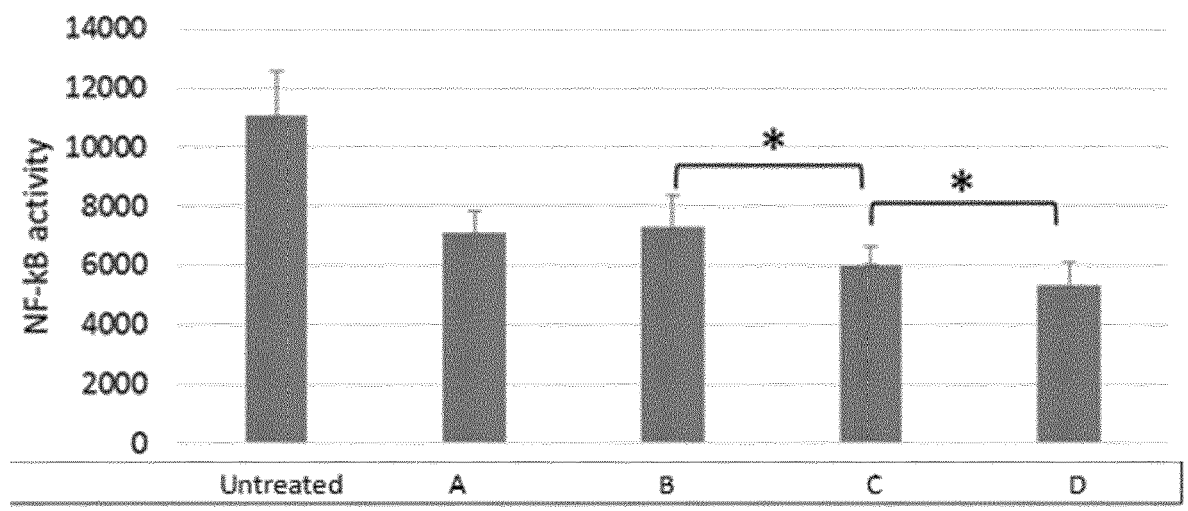

FIG. 12 shows the effect of the same mass of ESM particles with different mean particle diameters of on the inflammatory response of U937 human monocyte cells containing an NF-kB-controlled luciferase reporter construct to LPS as measured by NF-kB-activity. Untreated: ESM fragments larger than 1 mm; A & B: milled ESM particles less than 250 μm in size; C: milled ESM particles less than 120 μm in size; D: milled ESM particles less than 80 μm in size.

EXAMPLE 1

Antibacterial Activity of ESM
Introduction
Antibacterial activity of ESM particles (mean particle diameter 100 μm) was tested by measuring the growth curves of bacterial culture cultivated with/without ESM particles in an automated Bioscreen C system.

Materials and Method

*Escherichia coli* was cultivated on BHI agar (Brain heart infusion agar) for 24 hours at 37° C., and inoculum for the *Escherichia coli* was prepared by taking one colony from agar plate and re-suspending it into 5 ml of BHI broth. 10 µl of inoculum was thereafter inoculated in 350 µl of BHI broth and plated into honeycomb micro plates. Sterile BHI broth without inoculation of *E. coli* was used as a control.

A first cultivation without ESM particles in the automated Bioscreen C system was performed at 37° C. for 24 hours, with shaking before every measurement of OD600 (optical density). After 24 hours of cultivation autoclaved ESM particles (0.003 g and 0.01 g) was added to samples of *E. coli* and to the sterile broth. Sterile BHI broth with/without ESM particles was used as control.

Results and Conclusions

Figure 1:
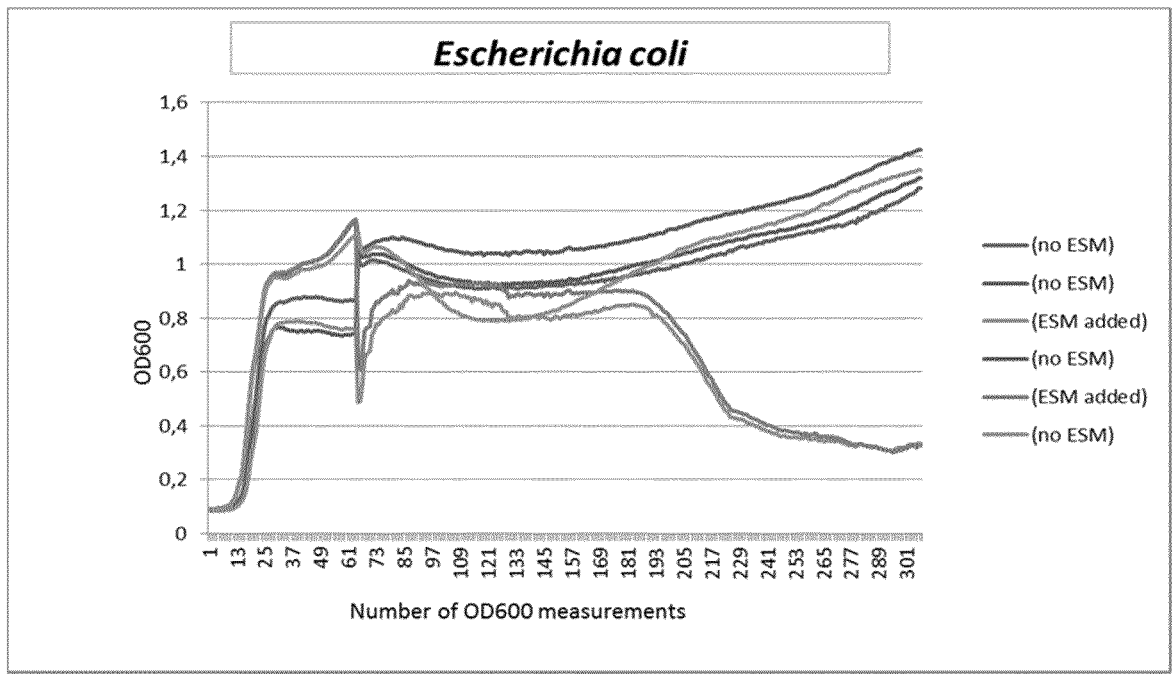

The growth curve after adding 0.003 g or 0.01 g of ESM particles was the same as for samples without ESM particles for 40 hrs, and thereafter decreased dramatically while samples without ESM particles showed increase. The results showed that ESM particles inhibit the viability and/or growth of *Escherichia coli* growth (FIG. 1).

EXAMPLE 2

Anti-Inflammatory Effect of ESM

Introduction

Transcriptional factor NF-kB plays an important role in stress and inflammatory response. U937 3×NF-kB-LUC cell system, a human monocyte cell line (U937) stably transfected with a 3×NF-kB-luciferase reporter construct, was used to investigate potential bioactivity of ESM particles (mean particle diameter 100 µm) on cellular inflammatory response by means of NF-kB expression.

Material and Method

Non adherent U937 3×NF-kB-LUC cells were seeded out in 96-wells titer plate in DMEM medium (Sigma) and cultured at 37° C. and 5% $CO_2$. The anti-inflammatory effect of ESM particles of different concentrations was tested (0 mg/ml, 0.5 and 1 mg/ml) by incubation 30 min prior to LPS treatment (1.0 µg/ml) for 5 hour to induce an inflammatory effect (proportional to luciferase activity). At the end of incubation luciferase activity was measured by use of the Bright-Glo Luciferase assay (Promega). In this assay, the lower the luciferase activity in response to LPS exposure, the greater the anti-inflammatory effect.

Results and Conclusions

Figure 2:
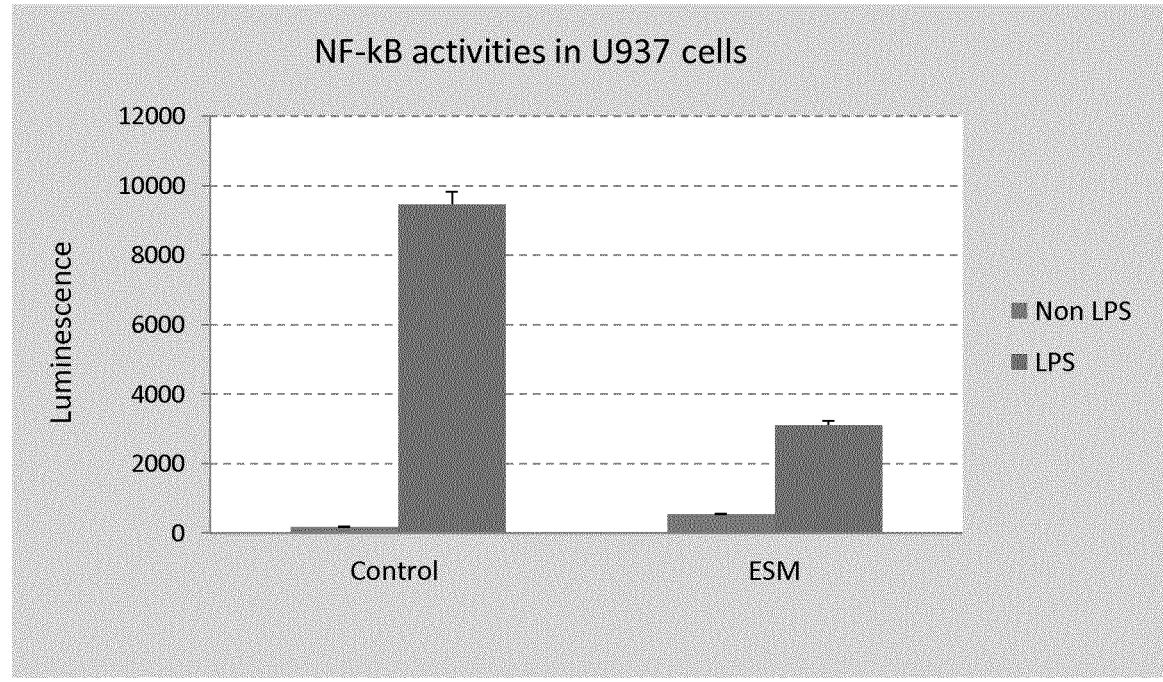

LPS induced inflammatory response was decreased in a dose dependent manner by ESM particles indicating an anti-inflammatory effect. FIG. 2 shows the effect of ESM particles at concentration of 1 mg/ml.

EXAMPLE 3

MMP Regulatory Effect

Introduction

Matrix metalloproteinases (MMPs) are a family of secreted or membrane-associated proteins capable of digesting extracellular matrix components. The effect of ESM particles (mean particle diameter 100 µm) on MMP-9 activity was tested by use of the SensoLyte® Generic MMP Assay Kit "Fluorometric" (AnaSpec). Screening of MMPs' inducers or inhibitors by use of recombinant MMPs is possible by this assay kit.

Material and Method

The SensoLyte® Generic MMP Assay Kit his kit uses a 5-FAM (fluorophore) and QXL520™ (quencher) labeled FRET peptide substrates for continuous measurement of the enzyme activities. In an intact FRET peptide, the fluorescence of 5-FAM is quenched by SensoLyte®. Upon the cleavage of the FRET peptide by MMPs, the fluorescence of 5-FAM is recovered, and can be continuously monitored at excitation/emission=490 nm/520 nm.

Different amounts of ESM particles were added to recombinant MMP-9 (AnaSpec) and the enzyme activity was measured according to the manufactures procedure. In addition, GM6001, a general inhibitor of MMP activity was used as a positive control for inhibition in the in vitro system.

Results and Conclusions

Figure 3:
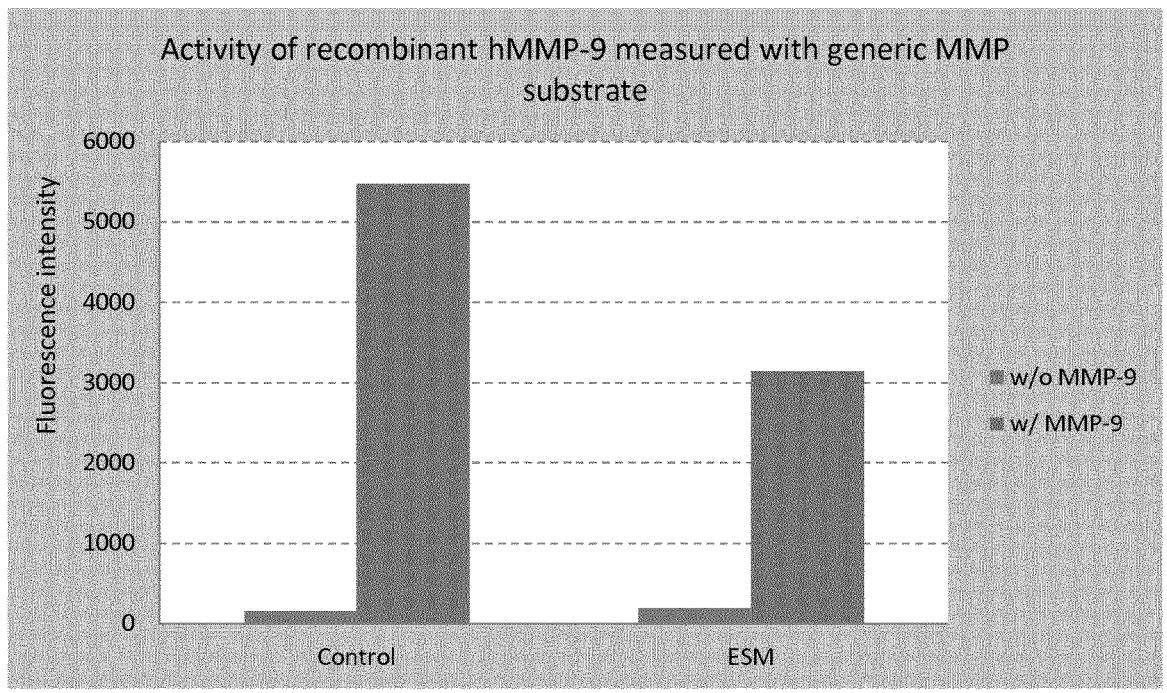
Figure 4:
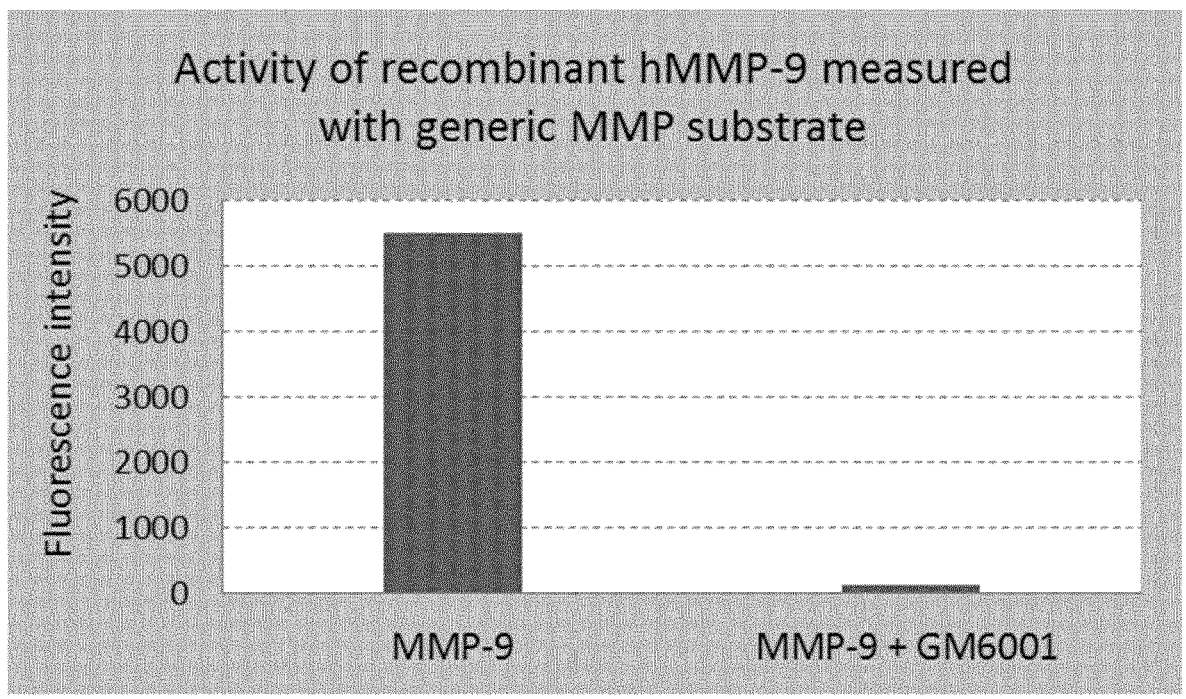
Figure 5:
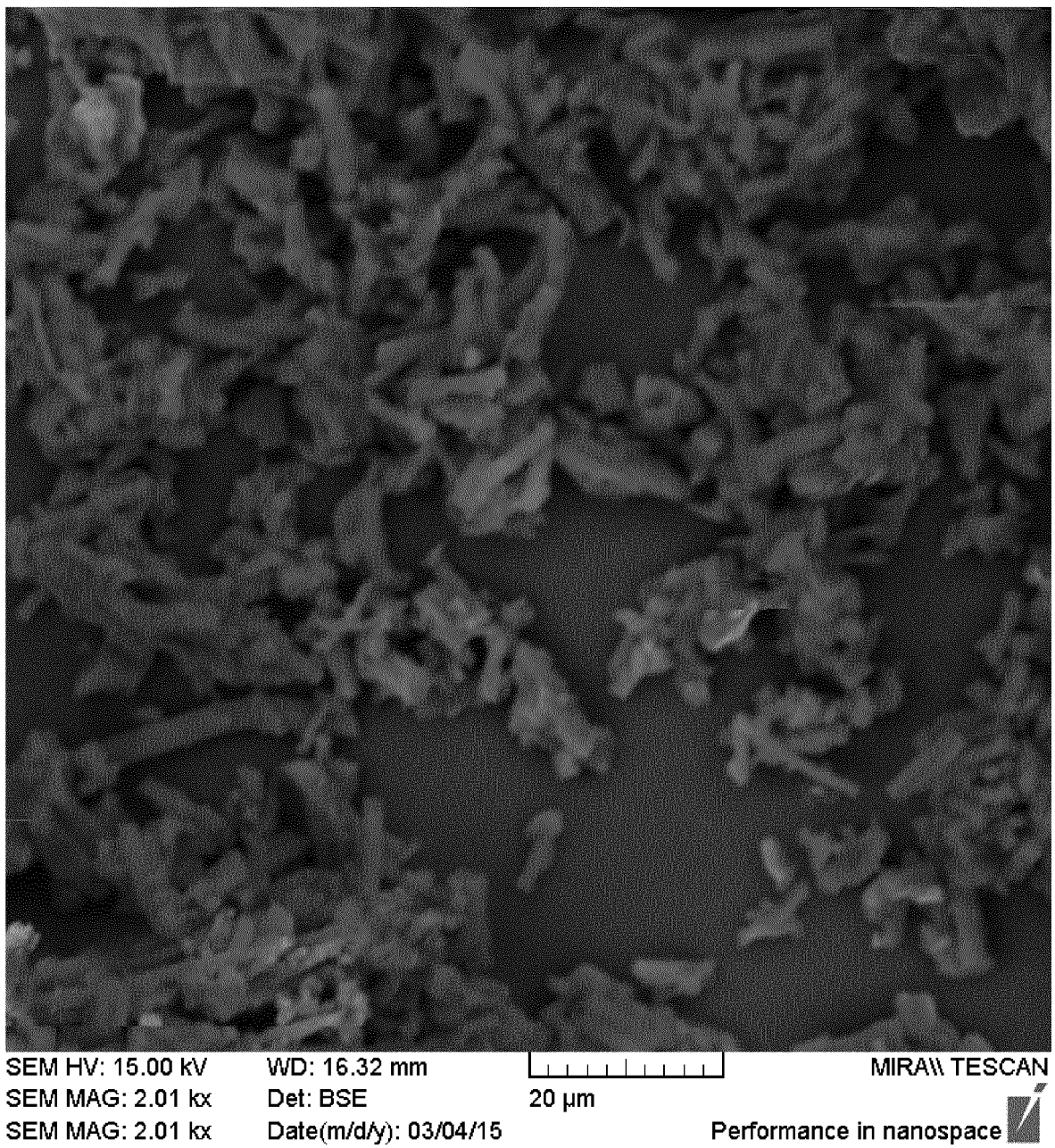

The activity of recombinant MMP-9 was decreased by adding ESM particles, indicating a negative effect of ESM particles on MMP activity (FIG. 3).

EXAMPLE 4

Preparation of Micronized ESM Particles for Application to a Wound

Following purification and milling, ESM is a low endotoxin and low bioburden material suitable for onward processing as a medical device. The dry powder formulation is manufactured by packaging the purified ESM material in 1 g sachets, for example fabricated from aluminium foil or Tyvec material. The sealed sachets are then sterilized by gamma irradiation (preferably 25 kGy).

The dry powder formulation may be applied to the wound surface by sprinkling the powder so as to cover the wound surface to a layer of 0.5 mm or less. ESM does not have intrinsic moisture absorbance capacity so an additional wound dressing such as a hydrocolloid, an alginate or fibre dressing should be placed on top of the dressed wound. Similarly, for dry wounds where debridement is indicated, the wound surface should first be treated with a hydrogel formulation and then the dry powder ESM sprinkled on top of the hydrogel.

During treatment and at dressing changes, the ESM product may be easily washed off the wound by irrigation with saline solution or other physiological solution. This may be required during dressing changes or to inspect the wound for infection of healing status.

Optimally, the ESM treated wound is covered with a secondary dressing to maintain the ESM in place and to promote a moist environment for tissue regrowth. In high exudate wounds, it would be preferable to cover the wound with a high capacity dressing such as a hydrofibre dressing, for example Aquacel.

EXAMPLE 5

Production of Hydrocolloid ESM Particle Gel and Application

Hydrocolloid gels are used in the management of wounds and may be supplied as either soft or aqueous gels or firm and solid gels. Firm hydrogels are sold under the brand names of Granuflex and Duoderm. They have moderate fluid absorbancy and maintain a moist wound bed without inducing maceration to the wound bed and surrounding skin. In response to wetting, they swell and remain viscous and retain the absorbed fluid. Soft or aqueous hydrogels have been described in the art, such as in U.S. Pat. No. 5,503,847.

A functional hydrogel incorporating ESM can be manufactured from pectin, sodium carboxymethyl cellulose and propylene glycol. In this example, the concentration of pectin is between 0.05% and 1%, the concentration of CMC is between 2% and 4.5%, the concentration of propylene glycol is between 15-20% and the concentration of ESM is between 0.5% and 10%. Water makes up the remainder to 100% by weight. In this embodiment, the formulation is additionally capable of cleansing and debriding the wound and absorbing moderate quantities of exudate. These functions augment the activity of ESM which binds and/or deflects proteases from wound bed destruction and acts as a scaffold to allow cellular attachment and migration through the wound bed.

The pectin is first dispersed and solubilized within the water by moderate heating to approximately 50° C. The propylene glycol is then added with mixing followed by gradual addition of CMC with vigorous mixing. When cooled to 20-30° C., the ESM particles are added with mixing. Once mixed, the ESM particles are evenly dispersed as a suspension within the hydrocolloid. The gel is then dispensed in aluminium or similar tubes or sachets and sterilized by gamma irradiation, preferably 25 kGy. The gel may be stored at 5° C., refrigerated, or may be stored at room temperature.

The hydrocolloid formulation is ideally suited for wounds with a deep cavity or which may be tunneled beneath healthy skin. In the latter type of wound, the gel may be loaded into a syringe and then delivered to the cavity to ensure that all wound surfaces are covered.

In a further embodiment ESM particles may be formulated in a substantially pure water/hydroxyethylcellulose hydrogel. Such a formulation may be prepared by dissolving HEC in water with agitation or stirring and dispersing ESM within said aqueous HEC solution. The ESM-HEC hydrogel may then be packaged into convenient receptacles, e.g. into tubes or sachets, and then the filled receptacles may be sterilised with gamma irradiation at, e.g., 25 kGy.

Optimally, the wound is then covered with a secondary dressing, such as a semi-permeable membrane, to maintain a moist environment and to keep the hydrocolloid in place.

Solid or firm gel hydrocolloids may also be manufactured which incorporate a semi-permeable backing sheet which may act as a sterile barrier as well as functioning in management of moisture within the wound surface. Such solid materials may incorporate polymers or gums or resins or gelatin to ensure that the dressing adheres lightly to the wound surface. Such products would be suited to the treatment of lightly to moderately exuding non-cavity wounds. Such dressings would not require a secondary dressing to keep them in place or to provide an anti-microbial barrier.

Optionally, the hydrocolloid may contain alginate to increase the moisture capacity of the base matrix gel. This would be preferable in wounds with moderate to high exudate. Such basic alginate gels are described in U.S. Pat. No. 6,201,164.

EXAMPLE 6

Production of ESM Sodium Alginate Composite Granules

In this example, ESM particles of use in the invention (fibres) are combined with sodium alginate to form a granulated powder. The granules are relatively large particles of approx. 100-200 μm in diameter. This size range makes the product relatively easy to apply by distribution to the wound by manual sprinkling direct from the final package container. On contact with the wound, the alginate component absorbs fluid, wound exudate (which contains $Ca^{2+}$), and swells to a gel (in situ dressing). The ESM particles are then hydrated either directly from the wound or indirectly from the gel and contact the wound surface.

Specifically, granules are formed by combining 40% weight ESM particles and 60% weight of a 40% Na alginate solution. The combination is then mixed in a rotary drum mixer until a homogeneous consistency is obtained. The material resembles a wet cake. This is then transferred to a fluid bed dryer and air dried until the moisture is less than 5% weight by weight by the loss on drying test method or equivalent. The material then resembles a coarse crumb. This is then cone milled with a 200 μm sieve to produce granules of bound ESM and alginate of less than 200 μm. It may be further screened to remove smaller particles. The granulated product is then packaged and sterilized, preferably by gamma irradiation or by ethylene oxide treatment.

Additional materials such as carboxymethylcellulose or hydroxyethylcellulose may be incorporated into the granules to further modify the moisture retention properties of the composite.

EXAMPLE 7

Production of ESM Sodium Alginate Composite Pad

40% weight ESM particles and 60% weight of a 40% Na alginate solution is combined and mixed in a rotary drum mixer until a homogeneous consistency is obtained. The material resembles a wet cake. The wet cake is then packed into moulds and then freeze dried or vacuum dried to produce a pad. Drying proceeds until the moisture concentration is below 5% weight/weight by loss on drying.

On contact with the wound, the alginate component of the pad absorbs fluid, wound exudate (which contains $Ca^{2+}$), and swells to a gel (in situ dressing). The ESM particles are then hydrated either directly from the wound or indirectly from the gel and contact the wound surface.

The pad may also be combined with other materials to make hybrid dressings, for example dressings with water impermeable backings to prevent leakage from high exudate wounds.

Additional materials such as carboxymethylcellulose or hydroxyethylcellulose may be incorporated into the pad to further modify the moisture retention properties of the composite.

EXAMPLE 8

Production of ESM Calcium Alginate Composite Pad

In this example, ESM particles are combined with Na alginate in solution. The soluble alginate is then precipitated from solution by addition of $CaCl_2$, to form an insoluble gel matrix of Ca alginate in which ESM is distributed.

Specifically, dry ESM particles of use in the invention (fibres) are first suspended in water at 1% weight/volume and then combined with sufficient Na alginate powder to give a 2% weight/volume solution of alginate. The suspension may need heating to approximately 50° C. to dissolve the Na alginate. The suspension is then placed in moulds for curing. A 10% $CaCl_2$ solution is then added slowly to each mould to a final concentration of 2% and the products are allowed to fully cure for 24 hours at between 0-30° C. After 24 hours, the excess water liberated from the gel during curing and Ca alginate formation is removed by aspiration and the moulds are placed in a freeze dryer or vacuum dryer. Drying proceeds until the moisture concentration is below 5% weight/weight by loss on drying. The product is then packaged and sterilized, preferably by gamma irradiation or by ethylene oxide treatment.

The pad may also be combined with other materials to make hybrid dressings, for example dressings with water impermeable backings to prevent leakage from high exudate wounds.

Additional materials such as carboxymethylcellulose or hydroxyethylcellulose may be incorporated into the pad to further modify the moisture retention properties of the composite.

EXAMPLE 9

Production of ESM Calcium Alginate Composite Fibre

In this example, ESM particles are incorporated into Ca alginate fibres during a spinning manufacturing process. A mixture of sodium alginate and ESM is extruded through a spinneret into a $CaCl_2$ bath. The $CaCl_2$ treatment precipitates the alginate polymers into an insoluble fibre in which the ESM material is incorporated. Granules and beads could be formed analogously by using a suitable spraying means.

Specifically, a spinning solution is prepared from deionized water with a pH of approx. 7.0, Na alginate and ESM particles of use in the invention (fibres). The thickness and diameter of the final alginate fibres are defined by the viscosity of solution which in turn is dependent on concentration of the spinning solution. The ESM particles are first suspended in water at between 1% and 50% w/v and then Na alginate powder is added to a concentration of around 5-6% w/v. The suspension is mixed by shearing. The suspension may need heating to approximately 50° C. to dissolve the Na alginate. The mixture is then spun into a water bath containing 2% $CaCl_2$ to precipitate the alginate as a Ca complex (gel). During this process the ESM particles become dispersed within the Ca alginate matrix to form a composite fibrous structure.

The spun fibres may then be collected on a drum roller and further processed as described by Qin to modify their gel and absorbent properties. Ion exchange of $Ca^{2+}$ by $Na^+$ during washing processes results in fibres with increased moisture absorbency. Thus, fibres with a range of properties are obtained which are suitable for a wide range of wound types. Ion exchange with other cations (e.g. zinc and silver) may be performed to further functionalise the fibres.

The spun fibres may then be formed into a mesh by standard techniques as described by Qin (supra). The spun fibres may also be combined with other materials to make hybrid dressings, for example dressings with water impermeable backings to prevent leakage from high exudate wounds. These products may then be packaged and sterilized by gamma irradiation, for example, prior to use.

Additional materials such as carboxymethylcellulose or hydroxyethylcellulose may be incorporated into the fibres to further modify the moisture retention properties of the composite.

EXAMPLE 10

Investigation of the Impact of ESM Particles on the Healing of Full-Thickness Excisional Wounds in the db/db Diabetic Mouse Introduction This study in the diabetic (db/db) mouse model (i.e. BKS.Cg-m $Dock7^m$+/+$Lepr^{db}$/J mice)—a recognised, and widely used, animal model of delayed wound healing—was performed to evaluate four ESM particle formulations with regard to their ability to promote tissue repair in a recognised in vivo model of delayed wound healing with a view to their future application in wound management & tissue repair.

The healing response of wounds treated with each of the four formulations was compared to each other and to that of wounds exposed to (i) 'no treatment' (negative control) and (ii) positive control treatment (platelet-derived growth factor-BB [rh-PDGF-BB]+Transforming Growth Factor-alpha [rh-TGF-α] in 0.5% HPMC).

This Example details the impact of these four ESM particle preparations on wound closure (reduction in open wound area over time) of full-thickness excisional skin wounds in the diabetic mouse. Wound closure data were determined from scaled wound images taken of each wound at each assessment point. The area of a given wound, at a given time point, was expressed as a percentage of the area of that wound immediately after injury (i.e. day 0). The mean percentage wound area remaining (& standard error of mean) was calculated for each group and is displayed graphically in FIGS. 6 to 11.

TABLE 1

Treatment Regimes

| Tx Group | Treatment (BFD = Bioclusive Film Dressing) | Application of treatment (day) | Group name | "n" |
|---|---|---|---|---|
| 1 | BFD only | 0, (4), 8, 12 & 16 | Negative control | 10 |
| 2 | Powder formulation - 30 mg/wound | 0 & 4* | ESM-30 | 10 |
| 3 | Powder formulation - 10 mg/wound | 0 & 4* | ESM-10 | 10 |
| 4 | Re-suspended powder formulation 3 mg | 0 & 4* | ESM-3 | 11 |
| 5 | Re-suspended powder formulation 1 mg | 0 & 4* | ESM-1 | 10 |
| 6 | rh-PDGF-BB [10 μg] + rh-TGF-α [1ug] – (100 μl)in 0.5% HMPC + BFD | 0, 1, 2, 3, 4, 5 & 6 | Positive control | 10 |

*Note for treatment groups 2, 3, 4 & 5 treatment was concluded on day 4 - due to build-up of rigid product on the surface of wounds in receipt of ESM-30 and ESM-10. In order to standardise the study, treatment was concluded in all groups on day 4.

Materials and Methods

The ESM particles were all from the same batch of purified material, aliquoted with overage into 10 ml stoppered and crimped glass vials and sterilized by gamma irradiation (approx. 25 kGy). The 30 and 10 mg units were applied directly to the wound as a dry powder. The 3 and 1 mg aliquots were hydrated in 50 μl of water for injection and then pipetted onto the wound surface as a suspension.

The positive control was prepared in a 0.5% HPMC vehicle (Hydroxypropyl methyl cellulose, Sigma Aldrich, UK). 0.5 g of Hydroxy-propyl-methyl cellulose (HPMC) was dissolved in 100 ml distilled water with the aid of warming, stirring and cooling. Sodium hydroxide was added to bring the pH up to 7.0.

Figure 6:
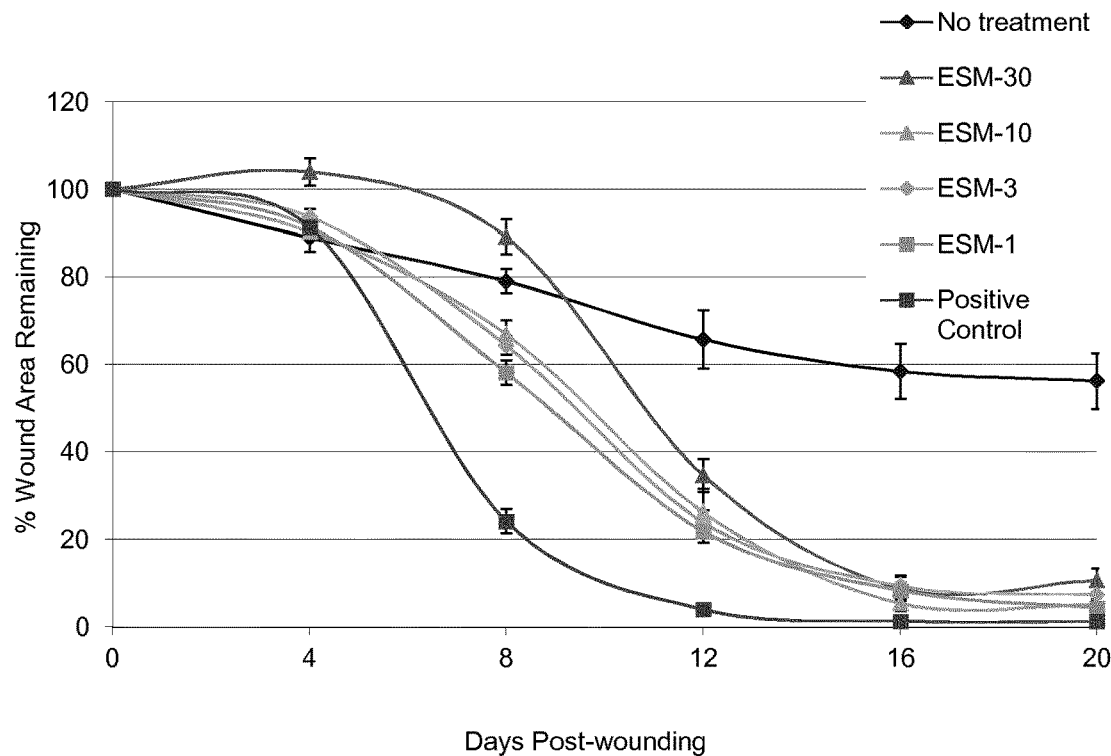
Figure 7:
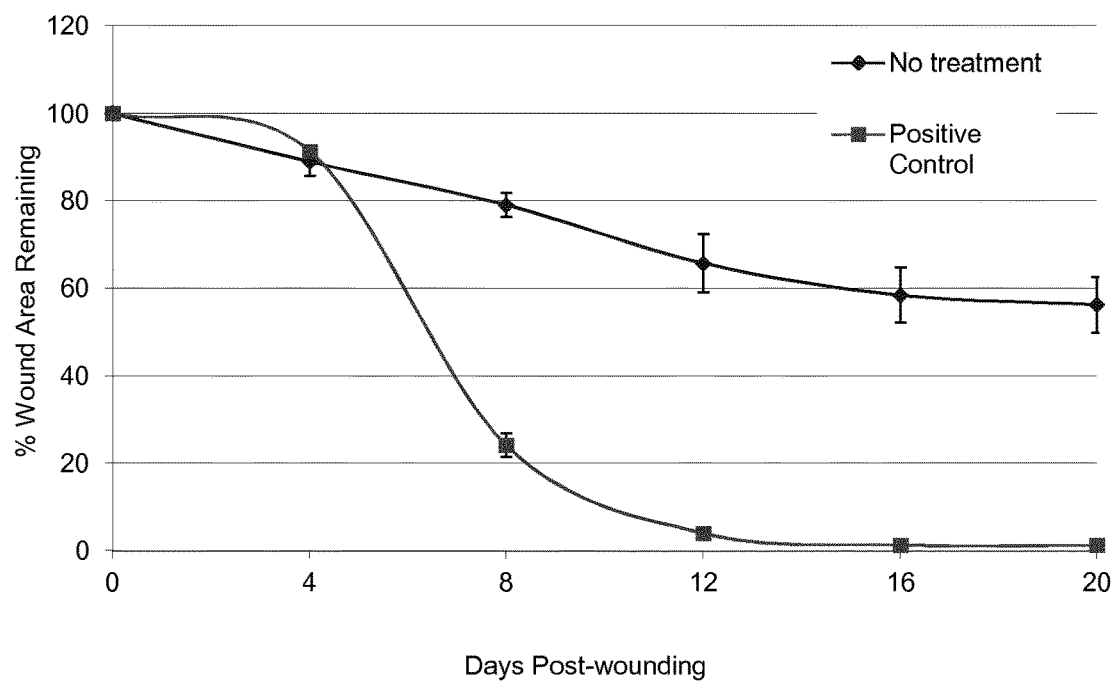
FIG. 7 shows the data from the negative and positive controls of FIG. 6.
Figure 8:
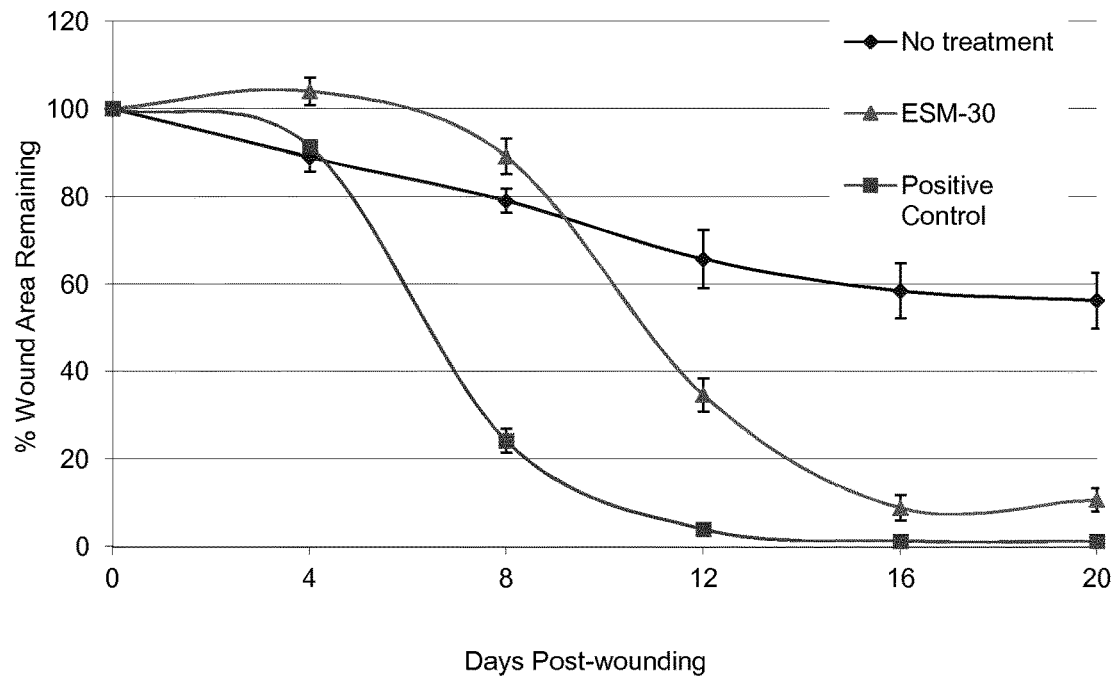
FIG. 8 shows the data from the negative and positive controls and ESM-30 of FIG. 6.
Figure 9:
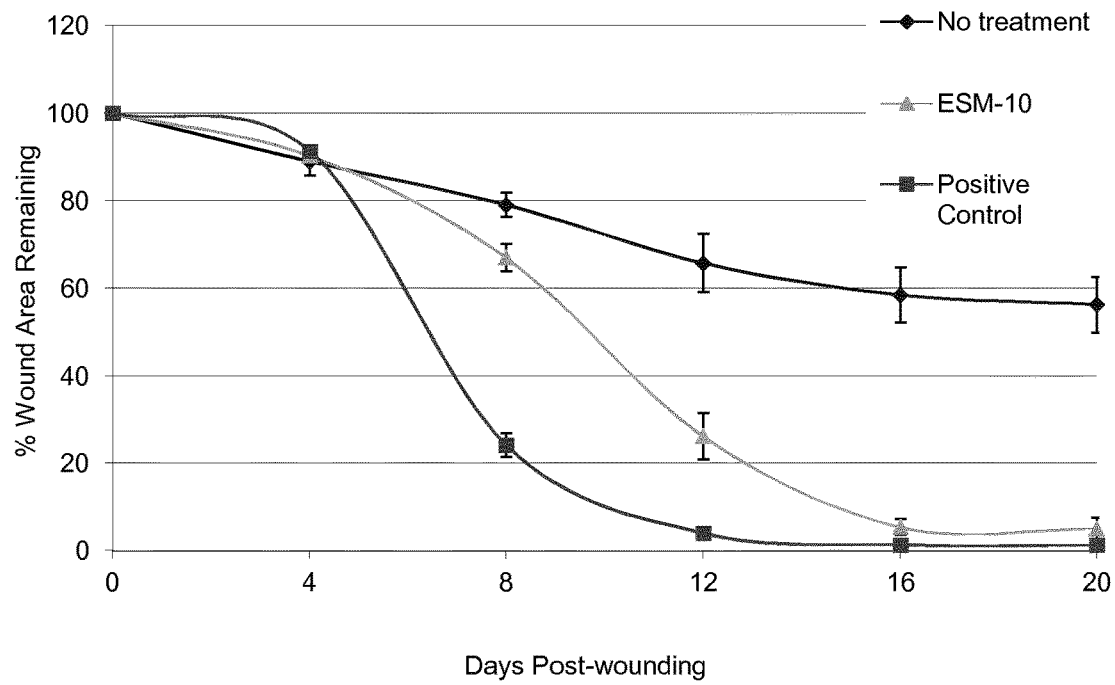
FIG. 9 shows the data from the negative and positive controls and ESM-10 of FIG. 6.
Figure 10:
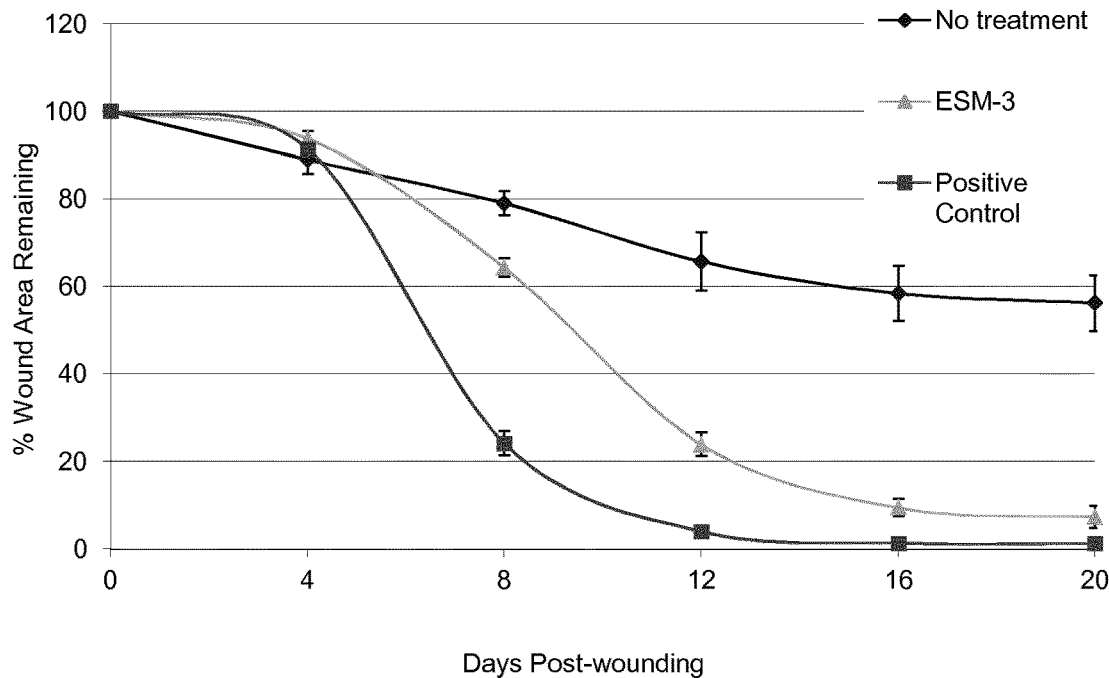
FIG. 10 shows the data from the negative and positive controls and ESM-3 of FIG. 6.
Figure 11:
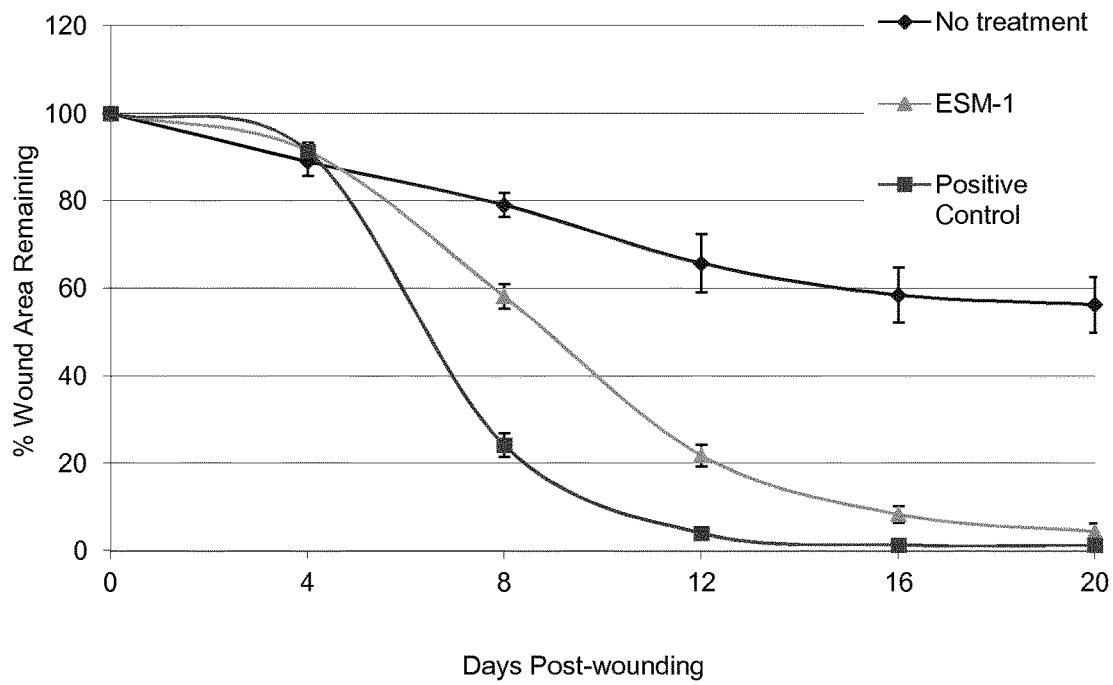
FIG. 11 shows the data from the negative and positive controls and ESM-1 of FIG. 6.

Results
1) Wound closure profiles of "% wound area remaining with time" data were found to differ noticeably between the different treatment groups (FIG. 6). Wounds in receipt of the growth factor combination (positive control) were found to display the fastest rate of closure—demonstrating close to full wound closure by day 16 post-wounding and significantly greater levels of wound closure relative to untreated wounds from day 8 onwards the study period (p=0.000, Mann-Whitney U test) (FIG. 7).

2) Wounds in receipt of ESM-30 were found to demonstrate an initial increase in wound area (observed on day 4). This was found to be statistically significant relative to untreated wounds (p≤0.02, Mann-Whitney U test). Wound closure (rather than wound expansion) was observed from day 8 onwards in this treatment group. The mean wound area, however, remained marginally greater than untreated wounds on day 8. Significantly increased wound closure relative to untreated wounds was observed from day 12 onwards (p≤0.005, Mann-Whitney U test) (FIG. 8).
3) Wounds in all other treatment groups: EMS-10, EMS-3 and EMS-1 were found to demonstrate significantly increased wound closure relative to untreated wounds from day 8 onwards (p≤0.000, Mann-Whitney U test) (FIGS. 9 to 11).
4) On comparison of the EMS treatment groups:
   i. Wounds in receipt of EMS-30 were found to be significantly larger than wounds in receipt of EMS-10 on days 4 and 8 (p=0.001).
   ii. Wounds in receipt of EMS-30 were found to be significantly larger than wounds in receipt of either EMS-3 or EMS-1 on days 4 to 12 (p=0.038).
   iii. On days 8 and 12 the lowest level of closure was observed with the highest concentration of ESM (ESM-30) and the greatest amount of wound closure was observed with the lowest concentration of ESM (ESM-1).
   iv. On day 8 the increase in wound closure observed with ESM-1 was found to be near significant compared to ESM-10 and ESM-3 (p=0.075 and p=0.063 respectively, Mann-Whitney, U test).
   v. A small increase in mean wound area remaining was observed with ESM-30 on day 20 compared to day 16.
5) No significant differences were observed between the positive control and i) ESM-10 on days 16 and 20 and ii) ESM-1 on day 20.

EXAMPLE 11

Anti-Inflammatory Effect of ESM Particles of Different Sizes

Material and Method

Non adherent U937 3×NF-kB-LUC cells were seeded out in 96-wells titer plate in DMEM medium (Sigma) and cultured at 37° C. and 5% $CO_2$. The anti-inflammatory effect of ESM particles of different sizes (less than 250 μm, less than 120 μm and less than 80 μm) was tested. A set mass of particles was applied to the cells 30 min prior to LPS treatment (1.0 μg/ml) for 5 hour to induce an inflammatory effect (proportional to luciferase activity). At the end of incubation luciferase activity was measured by use of the Bright-Glo Luciferase assay (Promega). In this assay, the lower the luciferase activity in response to LPS exposure, the greater the anti-inflammatory effect of the test substance.

Results and Conclusions

As shown in FIG. 12, there is an indirect relationship between ESM particle size and anti-inflammatory activity. Particles below 80 μm are more potent than particles above this size. Large particles or fragments of ESM of greater than 1 mm, labelled untreated in FIG. 12 have lowest activity.

The invention claimed is:

1. A method of promoting the healing of a non-healing chronic wound, wherein the non-healing chronic wound healing,
   (i) has not healed in 30 days after wound formation, and
   (ii) is stalled in the inflammatory stage of wound healing, wherein said method consists of applying directly to the surface or interior of the non-healing chronic wound a particle consisting of micronized egg shell membrane (ESM) having a mean particle diameter of equal to or less than 80 μm and being essentially insoluble in water at a neutral pH, and
   wherein the application of the particle to the non-healing chronic wound causes the non-healing chronic wounds to progress through the healing stages.

2. The method of claim 1, wherein said particle has a mean particle diameter of equal to or greater than 1 μm.

3. The method of claim 1, wherein said ESM is chicken, duck, goose, turkey, guineafowl, ostrich, pigeon, pheasant, partridge, grouse or gull ESM.

4. The method of claim 1, wherein said ESM is chemically non-degraded, non-digested and/or non-denatured as compared to naturally occurring ESM from a corresponding avian source.

5. The method of claim 1, wherein said ESM is non-hydrolysed.

6. The method of claim 1, wherein inflammation in the wound is reduced or limited following application of the particle to the wound.

7. The method of claim 1, wherein the viability and/or growth of a microorganism present in the wound is inhibited following application of the particle to the wound.

8. The method of claim 7, wherein said microorganism is selected from the genera *Citrobacter, Enterobacter, Escherichia, Hafnia, Serratia, Yersinia, Peptostreptococcus, Bacteroides, Pseudomonas, Legionella, Staphylococcus, Enterococcus, Streptococcus, Klebsiella, Candida, Proteus, Burkholderia, Fusobacterium* or *Mycobacterium*.

9. The method of claim 1, wherein the viability and/or growth of the cells of the wound tissue is promoted following application of the particle to the wound.

10. The method of claim 1, wherein the migration of the cells of the wound tissue into the wound is promoted following application of the particle to the wound.

11. The method of claim 1, wherein the wound is a skin wound and/or a wound containing an implantable medical device.

12. The method of claim 3, wherein said ESM is *Gallus domesticus* ESM.

13. The method of claim 8, wherein said microorganism is *Escherichia coli, Enterococcus faecalis Staphylococcus aureus, Staphylococcus epidermidis, Legionella pneumophila, Candida albicans, Pseudomonas aeruginosa, Burkholderia cepacia* or *Streptococcus pyogenes*.

* * * * *